(12) United States Patent
Teem

(10) Patent No.: US 6,468,793 B1
(45) Date of Patent: Oct. 22, 2002

(54) CFTR GENES AND PROTEINS FOR CYSTIC FIBROSIS GENE THERAPY

(75) Inventor: John L. Teem, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 0 days.

(21) Appl. No.: 09/425,453

(22) Filed: Oct. 22, 1999

Related U.S. Application Data

(60) Provisional application No. 60/105,444, filed on Oct. 23, 1998.

(51) Int. Cl.$^7$ .......................... C12N 15/00; C12N 15/63
(52) U.S. Cl. .................... 435/325; 435/69.1; 435/320.1; 536/23.1; 536/23.5
(58) Field of Search ............................... 536/23.1, 23.5; 530/350; 435/325, 252.1, 348, 320.1

(56) References Cited

U.S. PATENT DOCUMENTS

| | | | |
|---|---|---|---|
| 5,240,846 A | 8/1993 | Collins et al. |
| 5,399,346 A | 3/1995 | Anderson et al. |
| 5,543,399 A | 8/1996 | Riordan et al. |
| 5,639,661 A | 6/1997 | Welsh et al. |
| 5,670,488 A | 9/1997 | Gregory et al. |
| 5,827,703 A | 10/1998 | Debs et al. |

FOREIGN PATENT DOCUMENTS

| | | |
|---|---|---|
| WO | 9324641 | 12/1993 |

OTHER PUBLICATIONS

Alton, E.W. et al. (1999) "Cationic lipid–mediated CFTR gene transfer to the lungs and nose of patients with cystic fibrosis: a double–blind placebo–controlled trial" *Lancet* 353(9157):947–954.
Boat, T.F. et al. (1989) "Cystic Fibrosis. In the Metabolic Basis of Inherited Disease" C.R. Scriver, A.L. Beaudet, W.S. Sly and D. Valle, eds (New York, NY: McGraw–Hill, Inc.), pp. 2649–2680.
Flotte, T.R. et al. (1993) "Stable in vivo expression of the cystic fibrosis transmembrane conductance regulator with an adeno–associated virus vector" *Proc. Natl Acad Sci USA* 90:10613–10617.
Grubb, B.R. et al. (1994) "Inefficient gene transfer by adenovirus vector to cystic fibrosis airway epithelia of mice and humans" *Nature* 371:802–806.
Jiang, C. et al. (1998) "Efficiency of Cationic Lipid–Mediated Transfection of Polarized and Differentiated Airway Epithelial Cells In Vitro and In Vivo" *Human Gene Therapy* 9:1531–1542.
Kerem, B.–S. et al. (1989) "Identification of the Cystic Fibrosis Gene: Genetic Analysis" *Science* 245:1073–1080.
Riordan, J.R. et al. (1989) "Identification of the Cystic Fibrosis Gene: Cloning and Characterization of Complementary DNA" *Science* 245:1066–1073.

Rommens, J.M. et al. (1989) "Identification of the Cystic Fibrosis Gene: Chromosome Walking and Jumping" *Science* 245:1059–1065.
Rosenfeld, M.A. et al. (1992) "In Vivo Transfer of the Human Cystic Fibrosis Transmembrane Conductance Regulator Gene to the Airway Epithelium" *Cell* 68:143–155.
Sheppard, D.N. et al. (1993) "Mutations in CFTR associated with mild disease–form Cl$^-$ channels with altered pore properties" *Nature* 362:160–164.
Sheppard, D.N. et al. (1994) "Expression of cystic firbosis transmembrane conductance regulator in a model epithelium" *Am J Physiol* 266:405–413.
Teramoto, S. et al. (1998) "Factors Influencing Adeno–Associated Virus–Mediated Gene Transfer to Human Cystic Fibrosis Airway Epithelial Cells: Comparison with Adenovirus Vectors" *J Virol* 72:8904–8912.
Welsh, M.J. et al. (1993) "Molecular Mechanisms of CFTR Chloride Channel Dysfunction in Cystic Fibrosis" *Cell* 73:1251–1254.
Zabner, J. et al. (1993) "Adenovirus–Mediated Gene Transfer Transietly Corrects the Chloride Transport Defect in Nasal Epithelia of Patients with Cystic Fibrosis" *Cell* 75:207–216.
Zabner, J. et al. (1994) "Correction of cAMP–Stimulated Fluid Secretion in Cystic Fibrosis Airway Epithelia: Efficiency of Adenovirus–Mediated Gene Transfer In Vitro" *Human Gene Therapy* 5:585–593.1
Zabner, J. et al. (1994) "Safety and efficacy of representative adenovirus–mediated transfer of CFTR cDNA to airway epithelia of primated and cotton rats" *Nature Genetics* 6:75–83.

*Primary Examiner*—Dave T. Nguyen
(74) *Attorney, Agent, or Firm*—Saliwanchik, Lloyd & Saliwanchik

(57) ABSTRACT

The present invention pertains to mutated CFTR genes encoding modified CFTR proteins that result in increased CFTR chloride channel functions in comparison to wildtype CFTR when the CFTR genes are expressed in vivo. Single and multiple amino acid substitutions in a CFTR protein are contemplated in the present invention. The subject invention also concerns modified CFTR proteins encoded by the mutated genes of the invention. The subject invention also concerns methods for increasing CFTR chloride channel activity of a cell by delivering and expressing in the cell a polynucleotide or protein of the invention. The subject invention further concerns methods for treating patients with deficiencies in CFTR function. In one embodiment, the modified CFTR genes of the present invention can be used as a therapeutic agent delivered to CF cells by gene therapy. The modified CFTR genes of the present invention provide CFTR proteins with higher CFTR channel activity than that achievable with the wildtype CFTR gene when expressed in a cell.

28 Claims, 2 Drawing Sheets

SEQUENCE LISTING

<160> NUMBER OF SEQ ID NOS: 20

<210> SEQ ID NO 1
<211> LENGTH: 4443
<212> TYPE: DNA
<213> ORGANISM: Homo sapiens
<220> FEATURE:
<221> NAME/KEY: gene
<222> LOCATION: (1)..(4443)

<400> SEQUENCE: 1

```
atgcagaggt cgcctctgga aaaggccagc gttgtctcca aactttttt cagctggacc      60 agaccaattt tgaggaaagg atacagacag cgcctggaat tgtcagacat ataccaaatc     120
ccttctgttg attctgctga caatctatct gaaaaattgg aaagagaatg ggatagagag     180
ctggcttcaa agaaaaatcc taaactcatt aatgcccttc ggcgatgttt tttctggaga     240
tttatgttct atggaatctt tttatattta ggggaagtca ccaaagcagt acagcctctc     300
ttactgggaa gaatcatagc ttcctatgac ccggataaca aggaggaacg ctctatcgcg     360
atttatctag gcataggctt atgccttctc tttattgtga ggacactgct cctacaccca     420
gccatttttg gccttcatca cattggaatg cagatgagaa tagctatgtt tagtttgatt     480
tataagaaga ctttaaagct gtcaagccgt gttctagata aataagtat tggacaactt     540 gttagtctcc tttccaacaa cctgaacaaa tttgatgaag gacttgcatt ggcacatttc     600
gtgtggatcg ctcctttgca agtggcactc ctcatgggc taatctggga gttgttacag     660
gcgtctgcct tctgtggact tggtttcctg atagtccttg ccctttttca ggctgggcta     720
gggagaatga tgatgaagta cagagatcag agagctggga agatcagtga aagacttgtg     780
attacctcag aaatgattga aaatatccaa tctgttaagg catactgctg ggaagaagca     840
atggaaaaaa tgattgaaaa cttaagacaa acagaactga aactgactcg gaaggcagcc     900
```

```
tatgtgagat acttcaatag ctcagccttc ttcttctcag ggttctttgt ggtgttttta    960
tctgtgcttc cctatgcact aatcaaagga atcatcctcc ggaaaatatt caccaccatc   1020
tcattctgca ttgttctgcg catggcggtc actcggcaat ttccctgggc tgtacaaaca   1080
tggtatgact ctcttggagc aataaacaaa atacaggatt tcttacaaaa gcaagaatat   1140
aagacattgg aatataactt aacgactaca gaagtagtga tggagaatgt aacagccttc   1200
tgggaggagg gatttgggga attatttgag aaagcaaaac aaaacaataa caatagaaaa   1260
acttctaatg gtgatgacag cctcttcttc agtaatttct cacttcttgg tactcctgtc   1320
ctgaaagata ttaatttcaa gatagaaaga ggacagttgt tggcggttgc tggatccact   1380
ggagcaggca agacttcact tctaatgatg attatgggag aactggagcc ttcagagggt   1440
aaaattaagc acagtggaag aatttcattc tgttctcagt tttcctggat tatgcctggc   1500
accattaaag aaaatatcat ctttggtgtt tcctatgatg aatatagata cagaagcgtc   1560
atcaaagcat gccaactaga agaggacatc tccaagtttg cagagaaaga caatacagtt   1620
cttggagaag gtggaatcac actgagtgga ggtcaacgag caagaatttc tttagcaaga   1680
gcagtataca aagatgctga tttgtattta ttagactctc cttttggata cctagatgtt   1740
ttaacagaaa aagaaatatt tgaaagctgt gtctgtaaac tgatggctaa caaaactagg   1800
attttggtca cttctaaaat ggaacattta aagaaagctg acaaaatatt aattttgcat   1860
gaaggtagca gctattttta tgggacattt tcagaactcc aaaatctaca gccagctttt   1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa aacaatcttt taaacagact ggagagtttg gggaaaaaag gaagaattct   2100
attctcaatc caatcaactc tatacgaaaa ttttccattg tgcaaaagac tccttacaa    2160
atgaatggca tcgaagagga ttctgatgag cctttagaga aaggctgtc  cttagtacca   2220
gattctgagc agggagaggc gatactgcct cgcatcagcg tgatcagcac tggccccacg   2280
cttcaggcac gaaggaggca gtctgtcctg aacctgatga cacactcagt taaccaaggt   2340
cagaacattc accgaaagac aacagcatcc acacgaaaag tgtcactggc ccctcaggca   2400
aacttgactg aactggatat atattcaaga aggttatctc aagaaactgg cttggaaata   2460
agtgaagaaa ttaacgaaga agacttaaag gagtgctttt ttgatgatat ggagagcata   2520
ccagcagtga ctacatggaa cacatacctt cgatatatta ctgtccacaa gagcttaatt   2580
tttgtgctaa tttggtgctt agtaattttt ctggcagagg tggctgcttc tttggttgtg   2640
ctgtggctcc ttgaaacac  tcctcttcaa gacaaaggga atagtactca tagtagaaat   2700
aacagctatg cagtgattat caccagcacc agttcgtatt atgtgttttta catttacgtg   2760
ggagtagccg acactttgct tgctatggga ttcttcagag tctaccact ggtgcatact    2820
ctaatcacag tgtcgaaaat tttacaccac aaaatgttac attctgttct tcaagcacct   2880
atgtcaaccc tcaacacgtt gaaagcaggt gggattctta atagattctc caaagatata   2940
gcaattttgg atgaccttct gcctcttacc atatttgact tcatccagtt gttattaatt   3000
gtgattggag ctatagcagt tgtcgcagtt ttacaaccct acatctttgt tgcaacagtg   3060
ccagtgatag tggcttttat tatgttgaga gcatatttcc tccaaacctc acagcaactc   3120
aaacaactgg aatctgaagg caggagtcca atttcactc  atcttgttac aagcttaaaa   3180
ggactatgga cacttcgtgc cttcggacgg cagccttact ttgaaactct gttccacaaa   3240
gctctgaatt tacatactgc caactggttc ttgtacctgt caacactgcg ctggttccaa   3300
```

-continued

```
atgagaatag aaatgatttt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggccctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga aagcctttgg agtgatacca cagaaagtat ttattttttc tggaacattt    3900
agaaaaaact tggatcccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc aacaattttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
tag                                                                  4443
```

<210> SEQ ID NO 2
<211> LENGTH: 1480
<212> TYPE: PRT
<213> ORGANISM: Homo sapiens
<220> FEATURE:
<221> NAME/KEY: PEPTIDE
<222> LOCATION: (1)..(1480)

<400> SEQUENCE: 2

```
Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
             20                  25                  30

Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
     50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140
```

```
Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Ser Asn Asn Leu Asn Lys Phe Asp
                180                 185                 190

Glu Gly Leu Ala Leu Ala His Phe Val Trp Ile Ala Pro Leu Gln Val
                195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
        290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Thr Val Leu Gly Glu Gly
        530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
```

-continued

```
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu His Glu Gly Ser Ser
            610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
                660                 665                 670
Gly Asp Ala Pro Val Ser Trp Thr Glu Thr Lys Lys Gln Ser Phe Lys
                675                 680                 685
Gln Thr Gly Glu Phe Gly Glu Lys Arg Lys Asn Ser Ile Leu Asn Pro
            690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
                740                 745                 750
Ser Val Ile Ser Thr Gly Pro Thr Leu Gln Ala Arg Arg Arg Gln Ser
            755                 760                 765
Val Leu Asn Leu Met Thr His Ser Val Asn Gln Gly Gln Asn Ile His
    770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
                820                 825                 830
Leu Phe Asp Asp Met Glu Ser Ile Pro Ala Val Thr Thr Trp Asn Thr
            835                 840                 845
Tyr Leu Arg Tyr Ile Thr Val His Lys Ser Leu Ile Phe Val Leu Ile
850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
                900                 905                 910
Tyr Tyr Val Phe Tyr Ile Tyr Val Gly Val Ala Asp Thr Leu Leu Ala
            915                 920                 925
Met Gly Phe Phe Arg Gly Leu Pro Leu Val His Thr Leu Ile Thr Val
            930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
                980                 985                 990
```

-continued

Asp Phe Ile Gln Leu Leu Ile Val Ile Gly Ala Ile Ala Val Val
            995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
            1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
            1075                1080                1085

Trp Phe Leu Tyr Leu Ser Thr Leu Arg Trp Phe Gln Met Arg Ile Glu
            1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
            1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
    1155                1160                1165

Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
            1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
            1235                1240                1245

Gly Lys Ser Thr Leu Leu Ser Ala Phe Leu Arg Leu Leu Asn Thr Glu
1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
            1285                1290                1295

Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
            1315                1320                1325

Glu Gln Phe Pro Gly Lys Leu Asp Phe Val Leu Val Asp Gly Gly Cys
    1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
            1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
    1395                1400                1405

-continued

```
Glu Cys Gln Gln Phe Leu Val Ile Glu Asn Lys Val Arg Gln Tyr
    1410                1415                1420
Asp Ser Ile Gln Lys Leu Leu Asn Glu Arg Ser Leu Phe Arg Gln Ala
1425                1430                1435                1440
Ile Ser Pro Ser Asp Arg Val Lys Leu Phe Pro His Arg Asn Ser Ser
            1445                1450                1455
Lys Cys Lys Ser Lys Pro Gln Ile Ala Ala Leu Lys Glu Glu Thr Glu
        1460                1465                1470
Glu Glu Val Gln Asp Thr Arg Leu
    1475                1480
```

<210> SEQ ID NO 3
<211> LENGTH: 4443
<212> TYPE: DNA
<213> ORGANISM: Homo sapiens
<220> FEATURE:
<221> NAME/KEY: gene
<222> LOCATION: (1)..(4443)

<400> SEQUENCE: 3

| | | | | | |
|---|---|---|---|---|---|
| atgcagaggt | cgcctctgga | aaaggccagc | gttgtctcca | acttttttt | cagctggacc | 60 |
| agaccaattt | tgaggaaagg | atacagacag | cgcctggaat | tgtcagacat | ataccaaatc | 120 |
| ccttctgttg | attctgctga | caatctatct | gaaaaattgg | aaagagaatg | ggatagagag | 180 |
| ctggcttcaa | agaaaaatcc | taaactcatt | aatgcccttc | ggcgatgttt | tttctggaga | 240 |
| tttatgttct | atggaatctt | tttatattta | ggggaagtca | ccaaagcagt | acagcctctc | 300 |
| ttactgggaa | gaatcatagc | ttcctatgac | ccgataaca | aggaggaacg | ctctatcgcg | 360 |
| atttatctag | gcataggctt | atgccttctc | tttattgtga | ggacactgct | cctacaccca | 420 |
| gccattttg | gccttcatca | cattggaatg | cagatgagaa | tagctatgtt | tagtttgatt | 480 |
| tataagaaga | ctttaaagct | gtcaagccgt | gttctagata | aaataagtat | ggacaacttt | 540 |
| gttagtctcc | tttccaacaa | cctgaacaaa | tttgatgaag | acttgcatt | ggcacatttc | 600 |
| gtgtggatcg | ctccttttgca | agtggcactc | tcatggggc | taatctggga | gttgttacag | 660 |
| gcgtctgcct | tctgtggact | tggttcctg | atagtccttg | ccctttttca | ggctgggcta | 720 |
| gggagaatga | tgatgaagta | cagagatcag | agagctggga | agatcagtga | aagacttgtg | 780 |
| attacctcag | aaatgattga | aaatatccaa | tctgttaagg | catactgctg | ggaagaagca | 840 |
| atggaaaaaa | tgattgaaaa | cttaagacaa | acagaactga | aactgactcg | gaaggcagcc | 900 |
| tatgtgagat | acttcaatag | ctcagccttc | ttcttctcag | ggttctttgt | ggtgttttta | 960 |
| tctgtgcttc | cctatgcact | aatcaaagga | atcatcctcc | ggaaaatatt | caccaccatc | 1020 |
| tcattctgca | ttgttctgcg | catggcggtc | actcggcaat | tccctgggc | tgtacaaaca | 1080 |
| tggtatgact | ctcttggagc | aataaacaaa | atacaggatt | tcttacaaaa | gcaagaatat | 1140 |
| aagacattgg | aatataactt | aacgactaca | gaagtagtga | tggagaatgt | aacagccttc | 1200 |
| tgggaggagg | gatttgggga | attatttgag | aaagcaaaac | aaaacaataa | caatagaaaa | 1260 |
| acttctaatg | gtgatgacag | cctcttcttc | agtaatttct | cacttcttgg | tactcctgtc | 1320 |
| ctgaaagata | ttaatttcaa | gatagaaaga | ggacagttgt | tggcggttgc | tggatccact | 1380 |
| ggagcaggca | agacttcact | tctaatgatg | attatgggag | aactggagcc | ttcagagggt | 1440 |
| aaaattaagc | acagtggaag | aatttcattc | tgttctcagt | ttcctggat | tatgcctggc | 1500 |
| accattaaag | aaaatatcat | ctttggtgtt | tcctatgatg | aatatagata | cagaagcgtc | 1560 |
| atcaaagcat | gccaactaga | agaggacatc | tccaagtttg | cagagaaaga | caatatggtt | 1620 |

-continued

```
cttggagaag gtggaatcac actgagtgga ggtcaacgag caagaatttc tttagcaaga   1680
gcagtataca aagatgctga tttgtattta ttagactctc cttttggata cctagatgtt   1740
ttaacagaaa aagaaatatt tgaaagctgt gtctgtaaac tgatggctaa caaaactagg   1800
attttggtca cttctaaaat ggaacattta agaaagctg acaaaatatt aattttgcat    1860
gaaggtagca gctatttta tgggacattt tcagaactcc aaaatctaca gccagacttt    1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa aacaatcttt taaacagact ggagagtttg gggaaaaaag gaagaattct   2100
attctcaatc caatcaactc tatacgaaaa ttttccattg tgcaaaagac tcccttacaa   2160
atgaatggca tcgaagagga ttctgatgag cctttagaga aaggctgtc cttagtacca    2220 gattctgagc agggagaggc gatactgcct cgcatcagcg tgatcagcac tggccccacg   2280
cttcaggcac gaaggaggca gtctgtcctg aacctgatga cacactcagt taaccaaggt   2340
cagaacattc accgaaagac aacagcatcc acacgaaaag tgtcactggc ccctcaggca   2400
aacttgactg aactggatat atattcaaga aggttatctc aagaaactgg cttggaaata   2460
agtgaagaaa ttaacgaaga agacttaaag gagtgctttt ttgatgatat ggagagcata   2520
ccagcagtga ctacatggaa cacatacctt cgatatatta ctgtccacaa gagcttaatt   2580
tttgtgctaa tttggtgctt agtaattttt ctggcagagg tggctgcttc tttggttgtg   2640
ctgtggctcc ttggaaacac tcctcttcaa gacaaaggga atagtactca tagtagaaat   2700
aacagctatg cagtgattat caccagcacc agttcgtatt atgtgtttta catttacgtg   2760
ggagtagccg acactttgct tgctatggga ttcttcagag gtctaccact ggtgcatact   2820
ctaatcacag tgtcgaaaat tttacaccac aaaatgttac attctgttct tcaagcacct   2880
atgtcaaccc tcaacacgtt gaaagcaggt gggattctta atagattctc caaagatata   2940
gcaattttgg atgaccttct gcctcttacc atatttgact tcatccagtt gttattaatt   3000
gtgattggag ctatagcagt tgtcgcagtt ttacaaccct acatctttgt tgcaacagtg   3060
ccagtgatag tggcttttat tatgttgaga gcatatttcc tccaaacctc acagcaactc   3120
aaacaactgg aatctgaagg caggagtcca atttttcactc atcttgttac aagcttaaaa   3180
ggactatgga cacttcgtgc cttcggacgg cagccttact ttgaaactct gttccacaaa   3240
gctctgaatt tacatactgc caactggttc ttgtacctgt caacactgcg ctggttccaa   3300
atgagaatag aaatgattttt tgtcatcttc ttcattgctg ttaccttcat ttccattta   3360 acaacaggag aaggagaagg aagagttggt attatcctga ctttagccat gaatatcatg   3420
agtacattgc agtgggctgt aaactccagc atagatgtgg atagcttgat gcgatctgtg   3480
agccgagtct ttaagttcat tgacatgcca acagaaggta aacctaccaa gtcaaccaaa   3540
ccatacaaga atggccaact ctcgaaagtt atgattattg agaattcaca cgtgaagaaa   3600
gatgacatct ggcccctcagg gggccaaatg actgtcaaag atctcacagc aaaatacaca   3660
gaaggtggaa atgccatatt agagaacatt tccttctcaa taagtcctgg ccagagggtg   3720
ggcctcttgg gaagaactgg atcagggaag agtactttgt tatcagcttt tttgagacta   3780
ctgaacactg aaggagaaat ccagatcgat ggtgtgtctt gggattcaat aactttgcaa   3840
cagtggagga aagcctttgg agtgatacca cagaaagtat ttatttttc tggaacattt   3900 agaaaaaact tggatcccta tgaacagtgg agtgatcaag aaatatggaa agttgcagat   3960
```

-continued

```
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
tag                                                                  4443
```

<210> SEQ ID NO 4
<211> LENGTH: 1480
<212> TYPE: PRT
<213> ORGANISM: Homo sapiens
<220> FEATURE:
<221> NAME/KEY: PEPTIDE
<222> LOCATION: (1)..(1480)

<400> SEQUENCE: 4

```
Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
                 20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
         50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270
```

-continued

```
Lys Ala Tyr Cys Trp Glu Glu Ala Met Glu Lys Met Ile Glu Asn Leu
            275                 280                 285
Arg Gln Thr Glu Leu Lys Leu Thr Arg Lys Ala Ala Tyr Val Arg Tyr
        290                 295                 300
Phe Asn Ser Ser Ala Phe Phe Ser Gly Phe Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
            340                 345                 350
Gln Phe Pro Trp Ala Val Gln Thr Trp Tyr Asp Ser Leu Gly Ala Ile
        355                 360                 365
Asn Lys Ile Gln Asp Phe Leu Gln Lys Gln Glu Tyr Lys Thr Leu Glu
370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
            420                 425                 430
Phe Ser Leu Leu Gly Thr Pro Val Leu Lys Asp Ile Asn Phe Lys Ile
        435                 440                 445
Glu Arg Gly Gln Leu Leu Ala Val Ala Gly Ser Thr Gly Ala Gly Lys
    450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
        515                 520                 525
Asp Ile Ser Lys Phe Ala Glu Lys Asp Asn Met Val Leu Gly Glu Gly
    530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
        595                 600                 605
His Leu Lys Lys Ala Asp Lys Ile Leu Ile Leu His Glu Gly Ser Ser
    610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
        675                 680                 685
```

-continued

```
Gln Thr Gly Glu Phe Gly Glu Lys Arg Lys Asn Ser Ile Leu Asn Pro
    690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
            740                 745                 750
Ser Val Ile Ser Thr Gly Pro Thr Leu Gln Ala Arg Arg Gln Ser
        755                 760                 765
Val Leu Asn Leu Met Thr His Ser Val Asn Gln Gly Gln Asn Ile His
    770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
            820                 825                 830
Leu Phe Asp Asp Met Glu Ser Ile Pro Ala Val Thr Thr Trp Asn Thr
        835                 840                 845
Tyr Leu Arg Tyr Ile Thr Val His Lys Ser Leu Ile Phe Val Leu Ile
    850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
            900                 905                 910
Tyr Tyr Val Phe Tyr Ile Tyr Val Gly Val Ala Asp Thr Leu Leu Ala
        915                 920                 925
Met Gly Phe Phe Arg Gly Leu Pro Leu Val His Thr Leu Ile Thr Val
    930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
            980                 985                 990
Asp Phe Ile Gln Leu Leu Leu Ile Val Ile Gly Ala Ile Ala Val Val
        995                 1000                1005
Ala Val Leu Gln Pro Tyr Ile Phe Val Ala Thr Val Pro Val Ile Val
    1010                1015                1020
Ala Phe Ile Met Leu Arg Ala Tyr Phe Leu Gln Thr Ser Gln Gln Leu
1025                1030                1035                1040
Lys Gln Leu Glu Ser Glu Gly Arg Ser Pro Ile Phe Thr His Leu Val
                1045                1050                1055
Thr Ser Leu Lys Gly Leu Trp Thr Leu Arg Ala Phe Gly Arg Gln Pro
            1060                1065                1070
Tyr Phe Glu Thr Leu Phe His Lys Ala Leu Asn Leu His Thr Ala Asn
        1075                1080                1085
Trp Phe Leu Tyr Leu Ser Thr Leu Arg Trp Phe Gln Met Arg Ile Glu
    1090                1095                1100
Met Ile Phe Val Ile Phe Phe Ile Ala Val Thr Phe Ile Ser Ile Leu
```

-continued

```
            1105                1110                1115                1120

Thr Thr Gly Glu Gly Glu Gly Arg Val Gly Ile Ile Leu Thr Leu Ala
                        1125                1130                1135

Met Asn Ile Met Ser Thr Leu Gln Trp Ala Val Asn Ser Ser Ile Asp
                1140                1145                1150

Val Asp Ser Leu Met Arg Ser Val Arg Val Phe Lys Phe Ile Asp
            1155                1160                1165

Met Pro Thr Glu Gly Lys Pro Thr Lys Ser Thr Lys Pro Tyr Lys Asn
            1170                1175                1180

Gly Gln Leu Ser Lys Val Met Ile Ile Glu Asn Ser His Val Lys Lys
        1185                1190                1195                1200

Asp Asp Ile Trp Pro Ser Gly Gly Gln Met Thr Val Lys Asp Leu Thr
                        1205                1210                1215

Ala Lys Tyr Thr Glu Gly Gly Asn Ala Ile Leu Glu Asn Ile Ser Phe
                1220                1225                1230

Ser Ile Ser Pro Gly Gln Arg Val Gly Leu Leu Gly Arg Thr Gly Ser
                1235                1240                1245

Gly Lys Ser Thr Leu Leu Ser Ala Phe Leu Arg Leu Leu Asn Thr Glu
                1250                1255                1260

Gly Glu Ile Gln Ile Asp Gly Val Ser Trp Asp Ser Ile Thr Leu Gln
        1265                1270                1275                1280

Gln Trp Arg Lys Ala Phe Gly Val Ile Pro Gln Lys Val Phe Ile Phe
                        1285                1290                1295

Ser Gly Thr Phe Arg Lys Asn Leu Asp Pro Tyr Glu Gln Trp Ser Asp
                        1300                1305                1310

Gln Glu Ile Trp Lys Val Ala Asp Glu Val Gly Leu Arg Ser Val Ile
                1315                1320                1325

Glu Gln Phe Pro Gly Lys Leu Asp Phe Val Leu Val Asp Gly Gly Cys
                1330                1335                1340

Val Leu Ser His Gly His Lys Gln Leu Met Cys Leu Ala Arg Ser Val
        1345                1350                1355                1360

Leu Ser Lys Ala Lys Ile Leu Leu Leu Asp Glu Pro Ser Ala His Leu
                        1365                1370                1375

Asp Pro Val Thr Tyr Gln Ile Ile Arg Arg Thr Leu Lys Gln Ala Phe
                1380                1385                1390

Ala Asp Cys Thr Val Ile Leu Cys Glu His Arg Ile Glu Ala Met Leu
                1395                1400                1405

Glu Cys Gln Gln Phe Leu Val Ile Glu Glu Asn Lys Val Arg Gln Tyr
            1410                1415                1420

Asp Ser Ile Gln Lys Leu Leu Asn Glu Arg Ser Leu Phe Arg Gln Ala
        1425                1430                1435                1440

Ile Ser Pro Ser Asp Arg Val Lys Leu Phe Pro His Arg Asn Ser Ser
                        1445                1450                1455

Lys Cys Lys Ser Lys Pro Gln Ile Ala Ala Leu Lys Glu Glu Thr Glu
                        1460                1465                1470

Glu Glu Val Gln Asp Thr Arg Leu
                1475                1480

<210> SEQ ID NO 5
<211> LENGTH: 4443
<212> TYPE: DNA
<213> ORGANISM: Homo sapiens

<400> SEQUENCE: 5
```

-continued

| | | |
|---|---|---|
| atgcagaggt cgcctctgga aaaggccagc gttgtctcca acttttttt cagctggacc | 60 |
| agaccaattt tgaggaaagg atacagacag cgcctggaat tgtcagacat ataccaaatc | 120 |
| ccttctgttg attctgctga caatctatct gaaaaattgg aaagagaatg ggatagagag | 180 |
| ctggcttcaa agaaaaatcc taaactcatt aatgcccttc ggcgatgttt tttctggaga | 240 |
| tttatgttct atggaatctt tttatattta ggggaagtca ccaaagcagt acagcctctc | 300 |
| ttactgggaa gaatcatagc ttcctatgac ccggataaca aggaggaacg ctctatcgcg | 360 |
| atttatctag gcataggctt atgccttctc tttattgtga ggacactgct cctacaccca | 420 |
| gccatttttg gccttcatca cattggaatg cagatgagaa tagctatgtt tagtttgatt | 480 |
| tataagaaga ctttaaagct gtcaagccgt gttctagata aataagtat tggacaactt | 540 |
| gttagtctcc tttccaacaa cctgaacaaa tttgatgaag acttgcatt ggcacatttc | 600 |
| gtgtggatcc tccttttgca gtggcactc tcatggggc taatctggga gttgttacag | 660 |
| gcgtctgcct tctgtggact tggtttcctg atagtccttg cccttttttca ggctgggcta | 720 |
| gggagaatga tgatgaagta cagagatcag agagctggga gatcagtga aagacttgtg | 780 |
| attacctcag aaatgattga aaatatccaa tctgttaagg catactgctg ggaagaagca | 840 |
| atggaaaaaa tgattgaaaa cttaagacaa acagaactga aactgactcg gaaggcagcc | 900 |
| tatgtgagat acttcaatag ctcagccttc ttcttctcag gttctttgt ggtgttttta | 960 |
| tctgtgcttc cctatgcact aatcaaagga atcatcctcc ggaaaatatt caccaccatc | 1020 |
| tcattctgca ttgttctgcg catggcgtc actcggcaat ttccctgggc tgtacaaaca | 1080 |
| tggtatgact ctcttggagc aataaacaaa atacaggatt tcttacaaaa gcaagaatat | 1140 |
| aagacattgg aatataactt aacgactaca gaagtagtga tggagaatgt aacagccttc | 1200 |
| tgggaggagg gatttgggga attatttgag aaagcaaaac aaaacaataa caatagaaaa | 1260 |
| acttctaatg tgtgatgacag cctcttcttc agtaatttct cacttcttgg tactcctgtc | 1320 |
| ctgaaagata ttaatttcaa gatagaaaga ggacagttgt tggcggttgc tggatccact | 1380 |
| ggagcaggca agacttcact tctaatgatg attatgggag aactggagcc ttcagagggt | 1440 |
| aaaattaagc acagtggaag aatttcattc tgttctcagt tttcctggat tatgcctggc | 1500 |
| accattaaag aaaatatcat ctttggtgtt tcctatgatg aatatagata cagaagcgtc | 1560 |
| atcaaagcat gccaactaga agaggacatc tccaagtttg cagagaaaga caatatagtt | 1620 |
| cttggagaag gtggaatcac actgagtgaa ggtcaacgag caagaatttc tttagcaaga | 1680 |
| gcagtataca aagatgctga tttgtattta ttagactctc cttttggata cctagatgtt | 1740 |
| ttaacagaaa agaaatatt tgaaagctgt gtctgtaaac tgatggctaa caaaactagg | 1800 |
| attttggtca cttctaaaat ggaacattta agaaagctg acaaaatatt aattttgcat | 1860 |
| gaaggtagca gctatttta tgggacattt tcagaactcc aaaatctaca gccgactttt | 1920 |
| agctcaaaac tcatgggatg tgattctttc gaccaattta gtgcagaaag aagaaattca | 1980 |
| atcctaactg agaccttaca ccgtttctca ttagaaggag atgctcctgt ctcctggaca | 2040 |
| gaaacaaaaa aacaatcttt taaacagact ggagagtttg gggaaaaaag gaagaattct | 2100 |
| attctcaatc caatcaactc tatacgaaaa ttttccattg tgcaaaagac tcccttacaa | 2160 |
| atgaatggca tcgaagagga ttctgatgag cctttagaga aaggctgtc cttagtacca | 2220 |
| gattctgagc aggagaggc gatactgcct cgcatcagcg tgatcagcac tggccccacg | 2280 |
| cttcaggcac gaaggaggca gtctgtcctg aacctgatga cacactcagt taaccaaggt | 2340 |
| cagaacattc accgaaagac aacagcatcc acacgaaaag tgtcactggc ccctcaggca | 2400 |

```
aacttgactg aactggatat atattcaaga aggttatctc aagaaactgg cttggaaata    2460
agtgaagaaa ttaacgaaga agacttaaag gagtgctttt ttgatgatat ggagagcata    2520
ccagcagtga ctacatggaa cacatacctt cgatatatta ctgtccacaa gagcttaatt    2580
tttgtgctaa tttggtgctt agtaattttt ctggcagagg tggctgcttc tttggttgtg    2640
ctgtggctcc ttgaaacac tcctcttcaa gacaaaggga atagtactca tagtagaaat    2700
aacagctatg cagtgattat caccagcacc agttcgtatt atgtgtttta catttacgtg    2760
ggagtagccg acactttgct tgctatggga ttcttcagag gtctaccact ggtgcatact    2820
ctaatcacag tgtcgaaaat tttacaccac aaaatgttac attctgttct tcaagcacct    2880
atgtcaaccc tcaacacgtt gaaagcaggt gggattctta atagattctc caaagatata    2940
gcaattttgg atgaccttct gcctcttacc atatttgact tcatccagtt gttattaatt    3000
gtgattggag ctatagcagt tgtcgcagtt ttacaaccct acatctttgt tgcaacagtg    3060
ccagtgatag tggcttttat tatgttgaga gcatatttcc tccaaaccct acagcaactc    3120
aaacaactgg aatctgaagg caggagtcca attttcactc atcttgttac aagcttaaaa    3180
ggactatgga cacttcgtgc cttcggacgg cagccttact ttgaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccatttta    3360
acaacaggaa aaggagaagg aagagttggt attatcctga cttttagccat gaatatcatg    3420 agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggccctcagg gggccaaatg actgtcaaag atctcacagc aaaatacaca    3660
gaaggtggaa atgccatatt agaaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga aagcctttgg agtgatacca cagaaagtat ttattttttc tggaacattt    3900
agaaaaaact tggatcccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
tag                                                                  4443
```

<210> SEQ ID NO 6
<211> LENGTH: 1480
<212> TYPE: PRT
<213> ORGANISM: Homo sapiens

<400> SEQUENCE: 6

-continued

```
Met Gln Arg Ser Pro Leu Glu Lys Ala Ser Val Ser Lys Leu Phe
  1               5                  10                  15

Phe Ser Trp Thr Arg Pro Ile Leu Arg Lys Gly Tyr Arg Gln Arg Leu
                 20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
         50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
        290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
```

-continued

```
              420                 425                 430
Phe Ser Leu Leu Gly Thr Pro Val Leu Lys Asp Ile Asn Phe Lys Ile
            435                 440                 445
Glu Arg Gly Gln Leu Leu Ala Val Ala Gly Ser Thr Gly Ala Gly Lys
450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
                500                 505                 510
Asp Glu Tyr Arg Tyr Arg Ser Val Ile Lys Ala Cys Gln Leu Glu Glu
            515                 520                 525
Asp Ile Ser Lys Phe Ala Glu Lys Asp Asn Ile Val Leu Gly Glu Gly
            530                 535                 540
Gly Ile Thr Leu Ser Glu Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu His Glu Gly Ser Ser
            610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
                660                 665                 670
Gly Asp Ala Pro Val Ser Trp Thr Glu Thr Lys Lys Gln Ser Phe Lys
            675                 680                 685
Gln Thr Gly Glu Phe Gly Glu Lys Arg Lys Asn Ser Ile Leu Asn Pro
690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
                740                 745                 750
Ser Val Ile Ser Thr Gly Pro Thr Leu Gln Ala Arg Arg Arg Gln Ser
            755                 760                 765
Val Leu Asn Leu Met Thr His Ser Val Asn Gln Gly Gln Asn Ile His
            770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
                820                 825                 830
Leu Phe Asp Asp Met Glu Ser Ile Pro Ala Val Thr Thr Trp Asn Thr
            835                 840                 845
```

-continued

```
Tyr Leu Arg Tyr Ile Thr Val His Lys Ser Leu Ile Phe Val Leu Ile
    850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
            900                 905                 910
Tyr Tyr Val Phe Tyr Ile Tyr Val Gly Val Ala Asp Thr Leu Leu Ala
            915                 920                 925
Met Gly Phe Phe Arg Gly Leu Pro Leu Val His Thr Leu Ile Thr Val
    930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
            980                 985                 990
Asp Phe Ile Gln Leu Leu Leu Ile Val Ile Gly Ala Ile Ala Val Val
            995                 1000                1005
Ala Val Leu Gln Pro Tyr Ile Phe Val Ala Thr Val Pro Val Ile Val
    1010                1015                1020
Ala Phe Ile Met Leu Arg Ala Tyr Phe Leu Gln Thr Ser Gln Gln Leu
1025                1030                1035                1040
Lys Gln Leu Glu Ser Glu Gly Arg Ser Pro Ile Phe Thr His Leu Val
                1045                1050                1055
Thr Ser Leu Lys Gly Leu Trp Thr Leu Arg Ala Phe Gly Arg Gln Pro
            1060                1065                1070
Tyr Phe Glu Thr Leu Phe His Lys Ala Leu Asn Leu His Thr Ala Asn
            1075                1080                1085
Trp Phe Leu Tyr Leu Ser Thr Leu Arg Trp Phe Gln Met Arg Ile Glu
    1090                1095                1100
Met Ile Phe Val Ile Phe Phe Ile Ala Val Thr Phe Ile Ser Ile Leu
1105                1110                1115                1120
Thr Thr Gly Glu Gly Glu Gly Arg Val Gly Ile Ile Leu Thr Leu Ala
                1125                1130                1135
Met Asn Ile Met Ser Thr Leu Gln Trp Ala Val Asn Ser Ser Ile Asp
            1140                1145                1150
Val Asp Ser Leu Met Arg Ser Val Ser Arg Val Phe Lys Phe Ile Asp
            1155                1160                1165
Met Pro Thr Glu Gly Lys Pro Thr Lys Ser Thr Lys Pro Tyr Lys Asn
    1170                1175                1180
Gly Gln Leu Ser Lys Val Met Ile Ile Glu Asn Ser His Val Lys Lys
1185                1190                1195                1200
Asp Asp Ile Trp Pro Ser Gly Gly Gln Met Thr Val Lys Asp Leu Thr
                1205                1210                1215
Ala Lys Tyr Thr Glu Gly Gly Asn Ala Ile Leu Glu Asn Ile Ser Phe
            1220                1225                1230
Ser Ile Ser Pro Gly Gln Arg Val Gly Leu Leu Gly Arg Thr Gly Ser
            1235                1240                1245
Gly Lys Ser Thr Leu Leu Ser Ala Phe Leu Arg Leu Leu Asn Thr Glu
    1250                1255                1260
```

| Gly | Glu | Ile | Gln | Ile | Asp | Gly | Val | Ser | Trp | Asp | Ser | Ile | Thr | Leu | Gln |
|---|---|---|---|---|---|---|---|---|---|---|---|---|---|---|---|
| 1265 | | | | 1270 | | | | 1275 | | | | 1280 | | | |

| Gln | Trp | Arg | Lys | Ala | Phe | Gly | Val | Ile | Pro | Gln | Lys | Val | Phe | Ile | Phe |
|---|---|---|---|---|---|---|---|---|---|---|---|---|---|---|---|
| | | | 1285 | | | | 1290 | | | | 1295 | | | | |

| Ser | Gly | Thr | Phe | Arg | Lys | Asn | Leu | Asp | Pro | Tyr | Gln | Trp | Ser | Asp |
|---|---|---|---|---|---|---|---|---|---|---|---|---|---|---|
| | | 1300 | | | | 1305 | | | | 1310 | | | | |

| Gln | Glu | Ile | Trp | Lys | Val | Ala | Asp | Glu | Val | Gly | Leu | Arg | Ser | Val | Ile |
|---|---|---|---|---|---|---|---|---|---|---|---|---|---|---|---|
| | 1315 | | | | 1320 | | | | 1325 | | | | | | |

| Glu | Gln | Phe | Pro | Gly | Lys | Leu | Asp | Phe | Val | Leu | Val | Asp | Gly | Gly | Cys |
|---|---|---|---|---|---|---|---|---|---|---|---|---|---|---|---|
| | 1330 | | | | 1335 | | | | 1340 | | | | | | |

| Val | Leu | Ser | His | Gly | His | Lys | Gln | Leu | Met | Cys | Leu | Ala | Arg | Ser | Val |
|---|---|---|---|---|---|---|---|---|---|---|---|---|---|---|---|
| 1345 | | | | 1350 | | | | 1355 | | | | 1360 | | | |

| Leu | Ser | Lys | Ala | Lys | Ile | Leu | Leu | Leu | Asp | Glu | Pro | Ser | Ala | His | Leu |
|---|---|---|---|---|---|---|---|---|---|---|---|---|---|---|---|
| | | 1365 | | | | 1370 | | | | 1375 | | | | | |

| Asp | Pro | Val | Thr | Tyr | Gln | Ile | Ile | Arg | Arg | Thr | Leu | Lys | Gln | Ala | Phe |
|---|---|---|---|---|---|---|---|---|---|---|---|---|---|---|---|
| | | 1380 | | | | 1385 | | | | 1390 | | | | | |

| Ala | Asp | Cys | Thr | Val | Ile | Leu | Cys | Glu | His | Arg | Ile | Glu | Ala | Met | Leu |
|---|---|---|---|---|---|---|---|---|---|---|---|---|---|---|---|
| | | 1395 | | | | 1400 | | | | 1405 | | | | | |

| Glu | Cys | Gln | Gln | Phe | Leu | Val | Ile | Glu | Glu | Asn | Lys | Val | Arg | Gln | Tyr |
|---|---|---|---|---|---|---|---|---|---|---|---|---|---|---|---|
| 1410 | | | | 1415 | | | | 1420 | | | | | | | |

| Asp | Ser | Ile | Gln | Lys | Leu | Leu | Asn | Glu | Arg | Ser | Leu | Phe | Arg | Gln | Ala |
|---|---|---|---|---|---|---|---|---|---|---|---|---|---|---|---|
| 1425 | | | | 1430 | | | | 1435 | | | | 1440 | | | |

| Ile | Ser | Pro | Ser | Asp | Arg | Val | Lys | Leu | Phe | Pro | His | Arg | Asn | Ser | Ser |
|---|---|---|---|---|---|---|---|---|---|---|---|---|---|---|---|
| | | | 1445 | | | | 1450 | | | | 1455 | | | | |

| Lys | Cys | Lys | Ser | Lys | Pro | Gln | Ile | Ala | Ala | Leu | Lys | Glu | Glu | Thr | Glu |
|---|---|---|---|---|---|---|---|---|---|---|---|---|---|---|---|
| | | | 1460 | | | | 1465 | | | | 1470 | | | | |

| Glu | Glu | Val | Gln | Asp | Thr | Arg | Leu |
|---|---|---|---|---|---|---|---|
| | 1475 | | | | 1480 | | |

```
<210> SEQ ID NO 7
<211> LENGTH: 4443
<212> TYPE: DNA
<213> ORGANISM: Homo sapiens
<220> FEATURE:
<221> NAME/KEY: gene
<222> LOCATION: (1)..(4443)

<400> SEQUENCE: 7
atgcagaggt cgcctctgga aaaggccagc gttgtctcca aacttttttt cagctggacc      60
agaccaattt tgaggaaagg atacagacag cgcctggaat tgtcagacat ataccaaatc     120
ccttctgttg attctgctga caatctatct gaaaaattgg aaagagaatg ggatagagag     180
ctggcttcaa agaaaaatcc taaactcatt aatgcccttc ggcgatgttt tttctggaga     240
tttatgttct atggaatctt tttatattta ggggaagtca ccaaagcagt acagcctctc     300
ttactgggaa gaatcatagc ttcctatgac ccgataacaa ggaggaacg ctctatcgcg      360 atttatctag gcataggctt atgccttctc tttattgtga ggacactgct cctacaccca     420 gccattttg gccttcatca cattggaatg cagatgagaa tagctatgtt tagtttgatt      480
tataagaaga ctttaaagct gtcaagccgt gttctagata aataagtat tggacaactt      540 gttagtctcc tttccaacaa cctgaacaaa tttgatgaag acttgcatt ggcacatttc       600 gtgtggatcg ctcctttgca agtggcactc ctcatggggc taatctggga gttgttacag     660
gcgtctgcct tctgtggact tggtttcctg atagtccttg ccctttttca ggctgggcta     720
gggagaatga tgatgaagta cagagatcag agagctggga agatcagtga agacttgtg      780
```

| | |
|---|---|
| attacctcag aaatgattga aaatatccaa tctgttaagg catactgctg ggaagaagca | 840 |
| atggaaaaaa tgattgaaaa cttaagacaa acagaactga aactgactcg gaaggcagcc | 900 |
| tatgtgagat acttcaatag ctcagccttc ttcttctcag gttctttgt ggtgttttta | 960 |
| tctgtgcttc cctatgcact aatcaaagga atcatcctcc ggaaaatatt caccaccatc | 1020 |
| tcattctgca ttgttctgcg catggcggtc actcggcaat tccctgggc tgtacaaaca | 1080 |
| tggtatgact ctcttggagc aataaacaaa atacaggatt tcttacaaaa gcaagaatat | 1140 |
| aagacattgg aatataactt aacgactaca gaagtagtga tggagaatgt aacagccttc | 1200 |
| tgggaggagg gatttgggga attatttgag aaagcaaaac aaaacaataa caatagaaaa | 1260 |
| acttctaatg gtgatgacag cctcttcttc agtaatttct cacttcttgg tactcctgtc | 1320 |
| ctgaaagata ttaatttcaa gatagaaaga ggacagttgt tggcggttgc tggatccact | 1380 |
| ggagcaggca agacttcact tctaatgatg attatgggag aactggagcc ttcagagggt | 1440 |
| aaaattaagc acagtggaag aatttcattc tgttctcagt tttcctggat tatgcctggc | 1500 |
| accattaaag aaaatatcat ctttggtgtt tcctatgatg aatatagata cagaagcgtc | 1560 |
| atcaaagcat gccaactaga agaggacatc tccaagtttg cagagaaaga caatatagtt | 1620 |
| cttggagaag gtggaatcac actgagtgga ggtcaaatgg caagaatttc tttagcaaga | 1680 |
| gcagtataca aagatgctga tttgtattta ttagactctc cttttggata cctagatgtt | 1740 |
| ttaacagaaa aagaaatatt tgaaagctgt gtctgtaaac tgatggctaa caaaactagg | 1800 |
| attttggtca cttctaaaat ggaacattta aagaaagctg acaaaatatt aattttgcat | 1860 |
| gaaggtagca gctattttta tgggacattt tcagaactcc aaaatctaca gccagacttt | 1920 |
| agctcaaaac tcatgggatg tgattctttc gaccaattta gtgcagaaag aagaaattca | 1980 |
| atcctaactg agaccttaca ccgtttctca ttagaaggag atgctcctgt ctcctggaca | 2040 |
| gaaacaaaaa aacaatcttt taaacagact ggagagtttg gggaaaaaag gaagaattct | 2100 |
| attctcaatc caatcaactc tatacgaaaa ttttccattg tgcaaaagac tccccttacaa | 2160 |
| atgaatggca tcgaagagga ttctgatgag ccttttagaga aaggctgtc cttagtacca | 2220 |
| gattctgagc agggagaggc gatactgcct cgcatcagcg tgatcagcac tggccccacg | 2280 |
| cttcaggcac gaaggaggca gtctgtcctg aacctgatga cacactcagt taaccaaggt | 2340 |
| cagaacattc accgaaagac aacagcatcc acacgaaaag tgtcactggc ccctcaggca | 2400 |
| aacttgactg aactggatat atattcaaga aggttatctc aagaaactgg cttgaaaata | 2460 |
| agtgaagaaa ttaacgaaga agacttaaag gagtgctttt ttgatgatat ggagagcata | 2520 |
| ccagcagtga ctacatggaa cacataccct cgatatatta ctgtccacaa gagcttaatt | 2580 |
| tttgtgctaa tttggtgctt agtaattttt ctggcagagg tggctgcttc tttggttgtg | 2640 |
| ctgtggctcc ttgaaaacac tcctcttcaa gacaaaggga atagtactca tagtagaaat | 2700 |
| aacagctatg cagtgattat caccagcacc agttcgtatt atgtgttttta catttacgtg | 2760 |
| ggagtagccg acactttgct tgctatggga ttccttcagag gtctaccact ggtgcatact | 2820 |
| ctaatcacag tgtcgaaaat tttacaccac aaaatgttac attctgttct tcaagcacct | 2880 |
| atgtcaaccc tcaacacgtt gaaagcaggt gggattctta atagattctc caaagatata | 2940 |
| gcaattttgg atgaccttct gcctcttacc atatttgact tcatccagtt gttattaatt | 3000 |
| gtgattggag ctatagcagt tgtcgcagtt ttacaaccct acatctttgt tgcaacagtg | 3060 |
| ccagtgatag tggcttttat tatgttgaga gcatatttcc tccaaacctc acagcaactc | 3120 |
| aaacaactgg aatctgaagg caggagtcca attttcactc atcttgttac aagcttaaaa | 3180 |

-continued

```
ggactatgga cacttcgtgc cttcggacgg cagccttact ttgaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggccctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga agcctttgg agtgatacca cagaaagtat ttatttttc tggaacattt    3900 agaaaaaact tggatcccta tgaacagtgg agtgatcaag aaatatggaa agttgcagat    3960
gaggttgggc tcagatctgt gatagaacag tttcctggga agcttgactt tgtccttgtg    4020 gatggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380 aagcccaga ttgctgctct gaaagaggag acagaagaag aggtgcaaga tacaaggctt    4440
tag                                                                  4443
```

<210> SEQ ID NO 8
<211> LENGTH: 1480
<212> TYPE: PRT
<213> ORGANISM: Homo sapiens
<220> FEATURE:
<221> NAME/KEY: PEPTIDE
<222> LOCATION: (1)..(1480)

<400> SEQUENCE: 8

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125
```

```
Leu Leu Phe Ile Val Arg Thr Leu Leu His Pro Ala Ile Phe Gly
    130                 135                 140
Leu His His Ile Gly Met Gln Met Arg Ile Ala Met Phe Ser Leu Ile
145                 150                 155                 160
Tyr Lys Lys Thr Leu Lys Leu Ser Ser Arg Val Leu Asp Lys Ile Ser
                165                 170                 175
Ile Gly Gln Leu Val Ser Leu Ser Asn Asn Leu Asn Lys Phe Asp
                180                 185                 190
Glu Gly Leu Ala Leu Ala His Phe Val Trp Ile Ala Pro Leu Gln Val
            195                 200                 205
Ala Leu Leu Met Gly Leu Ile Trp Glu Leu Leu Gln Ala Ser Ala Phe
    210                 215                 220
Cys Gly Leu Gly Phe Leu Ile Val Leu Ala Leu Phe Gln Ala Gly Leu
225                 230                 235                 240
Gly Arg Met Met Met Lys Tyr Arg Asp Gln Arg Ala Gly Lys Ile Ser
                245                 250                 255
Glu Arg Leu Val Ile Thr Ser Glu Met Ile Glu Asn Ile Gln Ser Val
            260                 265                 270
Lys Ala Tyr Cys Trp Glu Glu Ala Met Glu Lys Met Ile Glu Asn Leu
            275                 280                 285
Arg Gln Thr Glu Leu Lys Leu Thr Arg Lys Ala Ala Tyr Val Arg Tyr
    290                 295                 300
Phe Asn Ser Ser Ala Phe Phe Phe Ser Gly Phe Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
                340                 345                 350
Gln Phe Pro Trp Ala Val Gln Thr Trp Tyr Asp Ser Leu Gly Ala Ile
            355                 360                 365
Asn Lys Ile Gln Asp Phe Leu Gln Lys Gln Glu Tyr Lys Thr Leu Glu
    370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
            420                 425                 430
Phe Ser Leu Leu Gly Thr Pro Val Leu Lys Asp Ile Asn Phe Lys Ile
            435                 440                 445
Glu Arg Gly Gln Leu Leu Ala Val Ala Gly Ser Thr Gly Ala Gly Lys
    450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
            485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
            515                 520                 525
Asp Ile Ser Lys Phe Ala Glu Lys Asp Asn Ile Val Leu Gly Glu Gly
    530                 535                 540
```

-continued

```
Gly Ile Thr Leu Ser Gly Gly Gln Met Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
                580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
        610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
                660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
        690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
                740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
        770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
        930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
```

-continued

```
                965                 970                 975
Ser Lys Asp Ile Ala Ile Leu Asp Asp Leu Leu Pro Leu Thr Ile Phe
                980                 985                 990

Asp Phe Ile Gln Leu Leu Leu Ile Val Ile Gly Ala Ile Ala Val Val
995                1000                1005

Ala Val Leu Gln Pro Tyr Ile Phe Val Ala Thr Val Pro Val Ile Val
1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
                1060                1065                1070

Tyr Phe Glu Thr Leu Phe His Lys Ala Leu Asn Leu His Thr Ala Asn
                1075                1080                1085

Trp Phe Leu Tyr Leu Ser Thr Leu Arg Trp Phe Gln Met Arg Ile Glu
                1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
                1140                1145                1150

Val Asp Ser Leu Met Arg Ser Val Ser Arg Val Phe Lys Phe Ile Asp
                1155                1160                1165

Met Pro Thr Glu Gly Lys Pro Thr Lys Ser Thr Lys Pro Tyr Lys Asn
                1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
                1220                1225                1230

Ser Ile Ser Pro Gly Gln Arg Val Gly Leu Leu Gly Arg Thr Gly Ser
                1235                1240                1245

Gly Lys Ser Thr Leu Leu Ser Ala Phe Leu Arg Leu Leu Asn Thr Glu
1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
                1285                1290                1295

Ser Gly Thr Phe Arg Lys Asn Leu Asp Pro Tyr Glu Gln Trp Ser Asp
                1300                1305                1310

Gln Glu Ile Trp Lys Val Ala Asp Glu Val Gly Leu Arg Ser Val Ile
                1315                1320                1325

Glu Gln Phe Pro Gly Lys Leu Asp Phe Val Leu Val Asp Gly Gly Cys
                1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
                1365                1370                1375

Asp Pro Val Thr Tyr Gln Ile Ile Arg Arg Thr Leu Lys Gln Ala Phe
                1380                1385                1390
```

```
Ala Asp Cys Thr Val Ile Leu Cys Glu His Arg Ile Glu Ala Met Leu
    1395                1400                1405
Glu Cys Gln Gln Phe Leu Val Ile Glu Asn Lys Val Arg Gln Tyr
    1410                1415                1420
Asp Ser Ile Gln Lys Leu Leu Asn Glu Arg Ser Leu Phe Arg Gln Ala
1425                1430                1435                1440
Ile Ser Pro Ser Asp Arg Val Lys Leu Phe Pro His Arg Asn Ser Ser
                1445                1450                1455
Lys Cys Lys Ser Lys Pro Gln Ile Ala Ala Leu Lys Glu Glu Thr Glu
            1460                1465                1470
Glu Glu Val Gln Asp Thr Arg Leu
    1475                1480

<210> SEQ ID NO 9
<211> LENGTH: 4443
<212> TYPE: DNA
<213> ORGANISM: Homo sapiens
<220> FEATURE:
<221> NAME/KEY: gene
<222> LOCATION: (1)..(4443)

<400> SEQUENCE: 9
```

| | | | | | |
|---|---|---|---|---|---|
| atgcagaggt | cgcctctgga | aaaggccagc | gttgtctcca | acttttttt | cagctggacc | 60 |
| agaccaattt | tgaggaaagg | atacagacag | cgcctggaat | tgtcagacat | ataccaaatc | 120 |
| ccttctgttg | attctgctga | caatctatct | gaaaaattgg | aaagagaatg | ggatagagag | 180 |
| ctggcttcaa | agaaaaatcc | taaactcatt | aatgcccttc | ggcgatgttt | tttctggaga | 240 |
| tttatgttct | atggaatctt | tttatattta | ggggaagtca | ccaaagcagt | acagcctctc | 300 |
| ttactgggaa | gaatcatagc | ttcctatgac | ccggataaca | aggaggaacg | ctctatcgcg | 360 |
| atttatctag | gcataggctt | atgccttctc | tttattgtga | ggacactgct | cctacaccca | 420 |
| gccattttg | gccttcatca | cattggaatg | cagatgagaa | tagctatgtt | tagtttgatt | 480 |
| tataagaaga | ctttaaagct | gtcaagccgt | gttctagata | aaataagtat | tggacaactt | 540 |
| gttagtctcc | tttccaacaa | cctgaacaaa | tttgatgaag | acttgcatt | ggcacatttc | 600 |
| gtgtggatcg | ctcctttgca | agtggcactc | ctcatggggc | taatctggga | gttgttacag | 660 |
| gcgtctgcct | tctgtggact | tggtttcctg | atagtccttg | cccttttca | ggctgggcta | 720 |
| gggagaatga | tgatgaagta | cagagatcag | agagctggga | agatcagtga | agacttgtg | 780 |
| attacctcag | aaatgattga | aaatatccaa | tctgttaagg | catactgctg | ggaagaagca | 840 |
| atggaaaaaa | tgattgaaaa | cttaagacaa | acagaactga | aactgactcg | gaaggcagcc | 900 |
| tatgtgagat | acttcaatag | ctcagccttc | ttcttctcag | ggttctttgt | ggtgttttta | 960 |
| tctgtgcttc | cctatgcact | aatcaaagga | atcatcctcc | ggaaaatatt | caccaccatc | 1020 |
| tcattctgca | ttgttctgcg | catggcggtc | actcggcaat | tccctgggc | tgtacaaaca | 1080 |
| tggtatgact | ctcttggagc | aataaacaaa | atacaggatt | tcttacaaaa | gcaagaatat | 1140 |
| aagacattgg | aatataactt | aacgactaca | gaagtagtga | tggagaatgt | aacagccttc | 1200 |
| tgggaggagg | gatttgggga | attatttgag | aaagcaaaac | aaaacaataa | caatagaaaa | 1260 |
| acttctaatg | gtgatgacag | cctcttcttc | agtaatttct | cacttcttgg | tactcctgtc | 1320 |
| ctgaaagata | ttaatttcaa | gatagaaaga | ggacagttgt | tggcggttgc | tggatccact | 1380 |
| ggagcaggca | agacttcact | tctaatgatg | attatggagg | aactggagcc | ttcagagggt | 1440 |
| aaaattaagc | acagtggaag | aatttcattc | tgttctcagt | tttcctggat | tatgcctggc | 1500 |

```
accattaaag aaaatatcat ctttggtgtt tcctatgatg aatatagata cagaagcgtc   1560
atcaaagcat gccaactaga agaggacatc tccaagtttg cagagaaaga caatatagtt   1620
cttggagaag gtggaatcac actgagtgga ggtcaacgag caaaaatttc tttagcaaga   1680
gcagtataca aagatgctga tttgtattta ttagactctc cttttggata cctagatgtt   1740
ttaacagaaa aagaaatatt tgaaagctgt gtctgtaaac tgatggctaa caaaactagg   1800
attttggtca cttctaaaat ggaacattta agaaagctg acaaaatatt aattttgcat    1860
gaaggtagca gctattttta tgggacattt tcagaactcc aaaatctaca gccagacttt   1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa aacaatcttt taaacagact ggagagtttg gggaaaaaag gaagaattct   2100
attctcaatc caatcaactc tatacgaaaa ttttccattg tgcaaaagac tcccttacaa   2160
atgaatggca tcgaagagga ttctgatgag cctttagaga aaggctgtc cttagtacca    2220 gattctgagc agggagaggc gatactgcct cgcatcagcg tgatcagcac tggccccacg   2280
cttcaggcac gaaggaggca gtctgtcctg aacctgatga cacactcagt taaccaaggt   2340
cagaacattc accgaaagac aacagcatcc acacgaaaag tgtcactggc ccctcaggca   2400
aacttgactg aactggatat atattcaaga aggttatctc aagaaactgg cttggaaata   2460
agtgaagaaa ttaacgaaga agacttaaag gagtgctttt ttgatgatat ggagagcata   2520
ccagcagtga ctacatggaa cacatacctt cgatatatta ctgtccacaa gagcttaatt   2580
tttgtgctaa tttggtgctt agtaattttt ctggcagagg tggctgcttc tttggttgtg   2640
ctgtggctcc ttggaaacac tcctcttcaa gacaaaggga atagtactca tagtagaaat   2700
aacagctatg cagtgattat caccagcacc agttcgtatt atgtgtttta catttacgtg   2760
ggagtagccg acactttgct tgctatggga ttcttcagag gtctaccact ggtgcatact   2820
ctaatcacag tgtcgaaaat tttacaccac aaaatgttac attctgttct tcaagcacct   2880
atgtcaaccc tcaacacgtt gaaagcaggt gggattctta atagattctc caaagatata   2940 gcaatttttgg atgaccttct gcctcttacc atatttgact tcatccagtt gttattaatt   3000
gtgattggag ctatagcagt tgtcgcagtt ttacaaccct acatctttgt tgcaacagtg   3060
ccagtgatag tggcttttat tatgttgaga gcatatttcc tccaaacctc acagcaactc   3120
aaacaactgg aatctgaagg caggagtcca attttcactc atcttgttac aagcttaaaa   3180
ggactatgga cacttcgtgc cttcggacgg cagccttact ttgaaactct gttccacaaa   3240
gctctgaatt tacatactgc caactggttc ttgtacctgt caacactgcg ctggttccaa   3300
atgagaatag aaatgatttt tgtcatcttc ttcattgctg ttaccttcat ttccatttta   3360
acaacaggag aaggagaagg aagagttggt attatcctga ctttagccat gaatatcatg   3420
agtacattgc agtgggctgt aaactccagc atagatgtgg atagcttgat gcgatctgtg   3480
agccgagtct ttaagttcat tgacatgcca acagaaggta aacctaccaa gtcaaccaaa   3540
ccatacaaga atggccaact ctcgaaagtt atgattattg agaattcaca cgtgaagaaa   3600
gatgacatct ggccctcagg gggccaaatg actgtcaaag atctcacagc aaaatacaca   3660
gaaggtggaa atgccatatt agagaacatt tccttctcaa taagtcctgg ccagagggtg   3720
ggcctcttgg gaagaactgg atcagggaag agtactttgt tatcagcttt tttgagacta   3780
ctgaacactg aaggagaaat ccagatcgat ggtgtgtctt gggattcaat aactttgcaa   3840
```

-continued

```
cagtggagga aagcctttgg agtgatacca cagaaagtat ttattttttc tggaacattt    3900
agaaaaaact tggatcccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
tag                                                                  4443
```

<210> SEQ ID NO 10
<211> LENGTH: 1480
<212> TYPE: PRT
<213> ORGANISM: Homo sapiens
<220> FEATURE:
<221> NAME/KEY: PEPTIDE
<222> LOCATION: (1)..(1480)

<400> SEQUENCE: 10

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
    65                  70                  75                  80

Phe Met Phe Tyr Gly Ile Phe Leu Tyr Leu Gly Glu Val Thr Lys Ala
                    85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                    165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
```

```
                     245                 250                     255
Glu Arg Leu Val Ile Thr Ser Glu Met Ile Glu Asn Ile Gln Ser Val
                260                 265                 270
Lys Ala Tyr Cys Trp Glu Ala Met Glu Lys Met Ile Glu Asn Leu
            275                 280                 285
Arg Gln Thr Glu Leu Lys Leu Thr Arg Lys Ala Ala Tyr Val Arg Tyr
        290                 295                 300
Phe Asn Ser Ser Ala Phe Phe Phe Ser Gly Phe Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
                340                 345                 350
Gln Phe Pro Trp Ala Val Gln Thr Trp Tyr Asp Ser Leu Gly Ala Ile
            355                 360                 365
Asn Lys Ile Gln Asp Phe Leu Gln Lys Gln Glu Tyr Lys Thr Leu Glu
        370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
                420                 425                 430
Phe Ser Leu Leu Gly Thr Pro Val Leu Lys Asp Ile Asn Phe Lys Ile
            435                 440                 445
Glu Arg Gly Gln Leu Leu Ala Val Ala Gly Ser Thr Gly Ala Gly Lys
        450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
        515                 520                 525
Asp Ile Ser Lys Phe Ala Glu Lys Asp Asn Ile Val Leu Gly Glu Gly
    530                 535                 540
Gly Ile Thr Leu Ser Gly Gly Gln Arg Ala Lys Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
        595                 600                 605
His Leu Lys Lys Ala Asp Lys Ile Leu Ile Leu His Glu Gly Ser Ser
    610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
                660                 665                 670
```

-continued

```
Gly Asp Ala Pro Val Ser Trp Thr Glu Thr Lys Lys Gln Ser Phe Lys
                675                 680                 685

Gln Thr Gly Glu Phe Gly Glu Lys Arg Lys Asn Ser Ile Leu Asn Pro
        690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
                740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
                820                 825                 830

Leu Phe Asp Asp Met Glu Ser Ile Pro Ala Val Thr Thr Trp Asn Thr
835                 840                 845

Tyr Leu Arg Tyr Ile Thr Val His Lys Ser Leu Ile Phe Val Leu Ile
850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
                900                 905                 910

Tyr Tyr Val Phe Tyr Ile Tyr Val Gly Val Ala Asp Thr Leu Leu Ala
                915                 920                 925

Met Gly Phe Phe Arg Gly Leu Pro Leu Val His Thr Leu Ile Thr Val
930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
                980                 985                 990

Asp Phe Ile Gln Leu Leu Leu Ile Val Ile Gly Ala Ile Ala Val Val
                995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
    1060                1065                1070

Tyr Phe Glu Thr Leu Phe His Lys Ala Leu Asn Leu His Thr Ala Asn
    1075                1080                1085
```

```
Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
        1155                1160                1165

Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
        1235                1240                1245

Gly Lys Ser Thr Leu Leu Ser Ala Phe Leu Arg Leu Leu Asn Thr Glu
    1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
                1285                1290                1295

Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
        1315                1320                1325

Glu Gln Phe Pro Gly Lys Leu Asp Phe Val Leu Val Asp Gly Gly Cys
    1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
                1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
        1395                1400                1405

Glu Cys Gln Gln Phe Leu Val Ile Glu Glu Asn Lys Val Arg Gln Tyr
    1410                1415                1420

Asp Ser Ile Gln Lys Leu Leu Asn Glu Arg Ser Leu Phe Arg Gln Ala
1425                1430                1435                1440

Ile Ser Pro Ser Asp Arg Val Lys Leu Phe Pro His Arg Asn Ser Ser
                1445                1450                1455

Lys Cys Lys Ser Lys Pro Gln Ile Ala Ala Leu Lys Glu Glu Thr Glu
            1460                1465                1470

Glu Glu Val Gln Asp Thr Arg Leu
        1475                1480

<210> SEQ ID NO 11
<211> LENGTH: 4443
<212> TYPE: DNA
```

<213> ORGANISM: Homo sapiens

<400> SEQUENCE: 11

```
atgcagaggt cgcctctgga aaaggccagc gttgtctcca aacttttttt cagctggacc      60
agaccaattt tgaggaaagg atacagacag cgcctggaat tgtcagacat ataccaaatc     120
ccttctgttg attctgctga caatctatct gaaaaattgg aaagagaatg ggatagagag     180
ctggcttcaa agaaaaatcc taaactcatt aatgcccttc ggcgatgttt tttctggaga     240
tttatgttct atggaatctt tttatattta ggggaagtca ccaaagcagt acagcctctc     300
ttactgggaa gaatcatagc ttcctatgac ccggataaca aggaggaacg ctctatcgcg     360
atttatctag gcataggctt atgccttctc tttattgtga ggacactgct cctacaccca     420
gccattttg gccttcatca cattggaatg cagatgagaa tagctatgtt tagtttgatt     480
tataagaaga ctttaaagct gtcaagccgt gttctagata aataagtat tggacaactt     540
gttagtctcc tttccaacaa cctgaacaaa tttgatgaag acttgcatt ggcacatttc     600
gtgtggatcg ctcctttgca agtggcactc ctcatggggc taatctggga gttgttacag     660
gcgtctgcct tctgtggact tggtttcctg atagtccttg ccctttttca ggctgggcta     720
gggagaatga tgatgaagta cagagatcag agagctggga agatcagtga aagacttgtg     780
attacctcag aaatgattga aaatatccaa tctgttaagg catactgctg ggaagaagca     840
atggaaaaaa tgattgaaaa cttaagacaa acagaactga aactgactcg gaaggcagcc     900
tatgtgagat acttcaatag ctcagccttc ttcttctcag gttctttgt ggtgtttta     960
tctgtgcttc cctatgcact aatcaaagga atcatcctcc ggaaaatatt caccaccatc    1020
tcattctgca ttgttctgcg catggcggtc actcggcaat ttccctgggc tgtacaaaca    1080
tggtatgact ctcttggagc aataaacaaa atacaggatt tcttacaaaa gcaagaatat    1140
aagacattgg aatataactt aacgactaca gaagtagtga tggagaatgt aacagccttc    1200
tgggaggagg gatttgggga attatttgag aaagcaaaac aaaacaataa caatagaaaa    1260
acttctaatg tgtgatgacag cctcttcttc agtaatttct cacttcttgg tactcctgtc    1320
ctgaaagata ttaatttcaa gatagaaaga ggacagttgt tggcggttgc tggatccact    1380
ggagcaggca agacttcact tctaatgatg attatgggag aactggagcc ttcagagggt    1440
aaaattaagc acagtggaag aatttcattc tgttctcagt tttcctggat tatgcctggc    1500
accattaaag aaaatatcat ctttggtgtt tcctatgatg aatatagata cagaagcgtc    1560
atcaaagcat gccaactaga agaggacatc tccaagtttg cagagaaaga caatacagtt    1620
cttggagaag gtggaatcac actgagtgaa ggtcaacgag caagaatttc tttagcaaga    1680
gcagtataca aagatgctga tttgtattta ttagactctc cttttggata cctagatgtt    1740
ttaacagaaa agaaatatt tgaaagctgt gtctgtaaac tgatggctaa caaaactagg    1800
attttggtca cttctaaaat ggaacattta agaaagctg acaaaatatt aattttgcat    1860
gaaggtagca gctattttta tgggacattt tcagaactcc aaaatctaca gccagctttt    1920
agctcaaaac tcatgggatg tgattctttc gaccaattta gtgcagaaag aagaaattca    1980
atcctaactg agaccttaca ccgtttctca ttagaaggag atgctcctgt ctcctggaca    2040
gaaacaaaaa aacaatcttt taaacagact ggagagtttg gggaaaaaag gaagaattct    2100
attctcaatc caatcaactc tatacgaaaa ttttccattg tgcaaagac tcccttacaa    2160
atgaatggca tcgaagagga ttctgatgag cctttagaga gaaggctgtc cttagtacca    2220
gattctgagc agggagaggc gatactgcct cgcatcagcg tgatcagcac tggccccacg    2280
```

-continued

```
cttcaggcac gaaggaggca gtctgtcctg aacctgatga cacactcagt taaccaaggt    2340
cagaacattc accgaaagac aacagcatcc acacgaaaag tgtcactggc cctcaggca     2400 aacttgactg aactggatat atattcaaga aggttatctc aagaaactgg cttggaaata   2460
agtgaagaaa ttaacgaaga agacttaaag gagtgctttt ttgatgatat ggagagcata   2520
ccagcagtga ctacatggaa cacataccct cgatatatta ctgtccacaa gagcttaatt   2580
tttgtgctaa tttggtgctt agtaattttt ctggcagagg tggctgcttc tttggttgtg   2640
ctgtggctcc ttgaaacac tcctcttcaa gacaaaggga atagtactca tagtagaaat    2700
aacagctatg cagtgattat caccagcacc agttcgtatt atgtgttta catttacgtg    2760 ggagtagccg acactttgct tgctatggga ttcttcagag gtctaccact ggtgcatact   2820
ctaatcacag tgtcgaaaat tttacaccac aaaatgttac attctgttct tcaagcacct   2880
atgtcaaccc tcaacacgtt gaaagcaggt gggattctta atagattctc caagatata    2940 gcaatttggg atgaccttct gcctcttacc atatttgact tcatccagtt gttattaatt   3000
gtgattggag ctatagcagt tgtcgcagtt ttacaaccct acatctttgt tgcaacagtg   3060
ccagtgatag tggcttttat tatgttgaga gcatatttcc tccaaacctc acagcaactc   3120
aaacaactgg aatctgaagg caggagtcca attttcactc atcttgttac aagcttaaaa   3180
ggactatgga cacttcgtgc cttcggacgg cagccttact ttgaaactct gttccacaaa   3240
gctctgaatt tacatactgc caactggttc ttgtacctgt caacactgcg ctggttccaa   3300
atgagaatag aaatgatttt tgtcatcttc ttcattgctg ttaccttcat ttccattta    3360 acaacaggaa aaggagaagg aagagttggt tattatcctga cttaggccat gaatatcatg   3420
agtacattgc agtgggctgt aaactccagc atagatgtgg atagcttgat gcgatctgtg   3480
agccgagtct ttaagttcat tgacatgcca acagaaggta aacctaccaa gtcaaccaaa   3540
ccatacaaga atggccaact ctcgaaagtt atgattattg agaattcaca cgtgaagaaa   3600
gatgacatct ggccctcagg gggccaaatg actgtcaaag atctcacagc aaaatacaca   3660
gaaggtggaa atgccatatt agagaacatt tccttctcaa taagtcctgg ccagagggtg   3720
ggcctcttgg gaagaactgg atcagggaag agtactttgt tatcagcttt tttgagacta   3780
ctgaacactg aaggagaaat ccagatcgat ggtgtgtctt gggattcaat aactttgcaa   3840
cagtggagga agcctttgg agtgatacca cagaaagtat ttatttttc tggaacattt     3900 agaaaaact tggatcccta tgaacagtgg agtgatcaag aaatatggaa agttgcagat    3960
gaggttgggc tcagatctgt gatagaacag tttcctggga agcttgactt tgtccttgtg   4020
gatgggggct gtgtcctaag ccatggccac aagcagttga tgtgcttggc tagatctgtt   4080
ctcagtaagg cgaagatctt gctgcttgat gaacccagtg ctcatttgga tccagtaaca   4140
taccaaataa ttagaagaac tctaaaacaa gcatttgctg attgcacagt aattctctgt   4200
gaacacagga tagaagcaat gctggaatgc caacaatttt tggtcataga agagaacaaa   4260
gtgcggcagt acgattccat ccagaaactg ctgaacgaga ggagcctctt ccggcaagcc   4320
atcagcccct ccgacagggt gaagctctt ccccaccgga actcaagcaa gtgcaagtct    4380
aagccccaga ttgctgctct gaaagaggag acagaagaag aggtgcaaga tacaaggctt   4440
tag                                                                 4443
```

<210> SEQ ID NO 12
<211> LENGTH: 1480
<212> TYPE: PRT

-continued

```
<213> ORGANISM: Homo sapiens

<400> SEQUENCE: 12

Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
             20                  25                  30

Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
     50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400
```

-continued

```
Trp Glu Glu Gly Phe Gly Glu Leu Phe Glu Lys Ala Lys Gln Asn Asn
            405                 410                 415
Asn Asn Arg Lys Thr Ser Asn Gly Asp Asp Ser Leu Phe Phe Ser Asn
        420                 425                 430
Phe Ser Leu Leu Gly Thr Pro Val Leu Lys Asp Ile Asn Phe Lys Ile
    435                 440                 445
Glu Arg Gly Gln Leu Leu Ala Val Ala Gly Ser Thr Gly Ala Gly Lys
450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
            485                 490                 495
Ile Met Pro Gly Thr Ile Lys Glu Asn Ile Ile Phe Gly Val Ser Tyr
                500                 505                 510
Asp Glu Tyr Arg Tyr Arg Ser Val Ile Lys Ala Cys Gln Leu Glu Glu
            515                 520                 525
Asp Ile Ser Lys Phe Ala Glu Lys Asp Asn Thr Val Leu Gly Glu Gly
    530                 535                 540
Gly Ile Thr Leu Ser Glu Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
            565                 570                 575
Tyr Leu Asp Val Leu Thr Glu Lys Glu Ile Phe Glu Ser Cys Val Cys
                580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu His Glu Gly Ser Ser
    610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
            645                 650                 655
Arg Arg Asn Ser Ile Leu Thr Glu Thr Leu His Arg Phe Ser Leu Glu
                660                 665                 670
Gly Asp Ala Pro Val Ser Trp Thr Glu Thr Lys Lys Gln Ser Phe Lys
            675                 680                 685
Gln Thr Gly Glu Phe Gly Glu Lys Arg Lys Asn Ser Ile Leu Asn Pro
    690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
            725                 730                 735
Ser Leu Val Pro Asp Ser Glu Gln Gly Glu Ala Ile Leu Pro Arg Ile
                740                 745                 750
Ser Val Ile Ser Thr Gly Pro Thr Leu Gln Ala Arg Arg Arg Gln Ser
            755                 760                 765
Val Leu Asn Leu Met Thr His Ser Val Asn Gln Gly Gln Asn Ile His
    770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
            805                 810                 815
Gly Leu Glu Ile Ser Glu Glu Ile Asn Glu Glu Asp Leu Lys Glu Cys
```

-continued

```
                    820                 825                 830
Leu Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
        1075                1080                1085

Trp Phe Leu Tyr Leu Ser Thr Leu Arg Trp Phe Gln Met Arg Ile Glu
    1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
                1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
        1155                1160                1165

Met Pro Thr Glu Gly Lys Pro Thr Lys Ser Thr Lys Pro Tyr Lys Asn
    1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
                1205                1210                1215

Ala Lys Tyr Thr Glu Gly Gly Asn Ala Ile Leu Glu Asn Ile Ser Phe
            1220                1225                1230

Ser Ile Ser Pro Gly Gln Arg Val Gly Leu Leu Gly Arg Thr Gly Ser
        1235                1240                1245
```

```
Gly Lys Ser Thr Leu Leu Ser Ala Phe Leu Arg Leu Leu Asn Thr Glu
    1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
            1285                1290                1295

Ser Gly Thr Phe Arg Lys Asn Leu Asp Pro Tyr Glu Gln Trp Ser Asp
        1300                1305                1310

Gln Glu Ile Trp Lys Val Ala Asp Glu Val Gly Leu Arg Ser Val Ile
        1315                1320                1325

Glu Gln Phe Pro Gly Lys Leu Asp Phe Val Leu Val Asp Gly Gly Cys
    1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
            1365                1370                1375

Asp Pro Val Thr Tyr Gln Ile Ile Arg Arg Thr Leu Lys Gln Ala Phe
        1380                1385                1390

Ala Asp Cys Thr Val Ile Leu Cys Glu His Arg Ile Glu Ala Met Leu
        1395                1400                1405

Glu Cys Gln Gln Phe Leu Val Ile Glu Glu Asn Lys Val Arg Gln Tyr
    1410                1415                1420

Asp Ser Ile Gln Lys Leu Leu Asn Glu Arg Ser Leu Phe Arg Gln Ala
1425                1430                1435                1440

Ile Ser Pro Ser Asp Arg Val Lys Leu Phe Pro His Arg Asn Ser Ser
            1445                1450                1455

Lys Cys Lys Ser Lys Pro Gln Ile Ala Ala Leu Lys Glu Glu Thr Glu
        1460                1465                1470

Glu Glu Val Gln Asp Thr Arg Leu
        1475                1480

<210> SEQ ID NO 13
<211> LENGTH: 4443
<212> TYPE: DNA
<213> ORGANISM: Homo sapiens

<400> SEQUENCE: 13
atgcagaggt cgcctctgga aaaggccagc gttgtctcca acttttttt cagctggacc      60 agaccaattt tgaggaaagg atacagacag cgcctggaat tgtcagacat ataccaaatc     120
ccttctgttg attctgctga caatctatct gaaaaattgg aaagagaatg ggatagagag     180
ctggcttcaa agaaaaatcc taaactcatt aatgcccttc ggcgatgttt tttctggaga     240
tttatgttct atggaatctt tttatattta ggggaagtca ccaaagcagt acagcctctc     300
ttactgggaa gaatcatagc ttcctatgac ccggataaca aggaggaacg ctctatcgcg     360
atttatctag gcataggctt atgccttctc tttattgtga ggacactgct cctacaccca     420 gccattttg gccttcatca cattggaatg cagatgagaa tagctatgtt tagtttgatt     480
tataagaaga ctttaaagct gtcaagccgt gttctagata aaataagtat ggacaacctt     540
gttagtctcc tttccaacaa cctgaacaaa tttgatgaag acttgcatt ggcacatttc     600 gtgtggatcg ctcctttgca gtggcactc ctcatgggc taatctggga gttgttacag     660
gcgtctgcct tctgtggact tggtttcctg atagtccttg cccttttca ggctgggcta     720 gggagaatga tgatgaagta cagagatcag agagctggga agatcagtga agacttgtg     780
```

-continued

```
attacctcag aaatgattga aaatatccaa tctgttaagg catactgctg ggaagaagca    840
atggaaaaaa tgattgaaaa cttaagacaa acagaactga aactgactcg gaaggcagcc    900
tatgtgagat acttcaatag ctcagccttc ttcttctcag ggttctttgt ggtgttttta    960
tctgtgcttc cctatgcact aatcaaagga atcatcctcc ggaaaatatt caccaccatc   1020
tcattctgca ttgttctgcg catggcggtc actcggcaat tccctgggc tgtacaaaca    1080
tggtatgact ctcttggagc aataaacaaa atacaggatt tcttacaaaa gcaagaatat   1140
aagacattgg aatataactt aacgactaca gaagtagtga tggagaatgt aacagccttc   1200
tgggaggagg gatttgggga attatttgag aaagcaaaac aaaacaataa caatagaaaa   1260
acttctaatg tgatgacag cctcttcttc agtaatttct cacttcttgg tactcctgtc    1320
ctgaaagata ttaatttcaa gatagaaaga ggacagttgt tggcggttgc tggatccact   1380
ggagcaggca agacttcact tctaatgatg attatgggag aactggagcc ttcagagggt   1440
aaaattaagc acagtggaag aatttcattc tgttctcagt tttcctggat tatgcctggc   1500
accattaaag aaaatatcat ctttggtgtt tcctatgatg aatatagata cagaagcgtc   1560
atcaaagcat gccaactaga agaggacatc tccaagtttg cagagaaaga caatacagtt   1620
cttggagaag gtggaatcac actgagtgga ggtcaaatgg caaaaatttc tttagcaaga   1680
gcagtataca agatgctga tttgtattta ttagactctc cttttggata cctagatgtt   1740
ttaacagaaa agaaatatt tgaaagctgt gtctgtaaac tgatggctaa caaaactagg   1800
attttggtca cttctaaaat ggaacattta agaaagctg acaaaatatt aattttgcat   1860
gaaggtagca gctattttta tgggacattt tcagaactcc aaaatctaca gccagacttt   1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa aacaatcttt taaacagact ggagagtttg gggaaaaaag gaagaattct   2100
attctcaatc caatcaactc tatacgaaaa ttttccattg tgcaaaagac tcccttacaa   2160
atgaatggca tcgaagagga ttctgatgag cctttagaga aaggctgtc cttagtacca   2220
gattctgagc agggagaggc gatactgcct cgcatcagcg tgatcagcac tggccccacg   2280
cttcaggcac gaaggaggca gtctgtcctg aacctgatga cacactcagt taaccaaggt   2340
cagaacattc accgaaagac aacagcatcc acacgaaaag tgtcactggc ccctcaggca   2400
aacttgactg aactggatat atattcaaga aggttatctc aagaaactgg cttggaaata   2460
agtgaagaaa ttaacgaaga agacttaaag gagtgctttt ttgatgatat ggagagcata   2520
ccagcagtga ctacatggaa cacataccct cgatatatta ctgtccacaa gagcttaatt   2580
tttgtgctaa tttggtgctt agtaattttt ctggcagagg tggctgcttc tttggttgtg   2640
ctgtggctcc ttgaaacac tcctcttcaa gacaaaggga atagtactca tagtagaaat   2700
aacagctatg cagtgattat caccagcacc agttcgtatt atgtgtttta catttacgtg   2760
ggagtagccg acactttgct tgctatggga ttcttcagag tctaccact ggtgcatact   2820
ctaatcacag tgtcgaaaat tttacaccac aaaatgttac attctgttct tcaagcacct   2880
atgtcaaccc tcaacacgtt gaaagcaggt gggattctta atagattctc caagatata   2940
gcaattttgg atgaccttct gcctcttacc atatttgact tcatccagtt gttattaatt   3000
gtgattggag ctatagcagt tgtcgcagtt ttacaaccct acatctttgt tgcaacagtg   3060
ccagtgatag tggcttttat tatgttgaga gcatatttcc tccaaacctc acagcaactc   3120
```

```
aaacaactgg aatctgaagg caggagtcca attttcactc atcttgttac aagcttaaaa    3180
ggactatgga cacttcgtgc cttcggacgg cagccttact ttgaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggccctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga aagcctttgg agtgatacca cagaaagtat ttatttttc tggaacattt    3900
agaaaaaact tggatcccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
tag                                                                 4443

<210> SEQ ID NO 14
<211> LENGTH: 1480
<212> TYPE: PRT
<213> ORGANISM: Homo sapiens

<400> SEQUENCE: 14

Met Gln Arg Ser Pro Leu Glu Lys Ala Ser Val Val Ser Lys Leu Phe
  1               5                  10                  15

Phe Ser Trp Thr Arg Pro Ile Leu Arg Lys Gly Tyr Arg Gln Arg Leu
                 20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
         50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
```

```
            130                 135                 140
Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
                195                 200                 205

Ala Leu Leu Met Gly Leu Ile Trp Glu Leu Leu Gln Ala Ser Ala Phe
            210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
                420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
                515                 520                 525

Asp Ile Ser Lys Phe Ala Glu Lys Asp Asn Thr Val Leu Gly Glu Gly
            530                 535                 540

Gly Ile Thr Leu Ser Gly Gly Gln Met Ala Lys Ile Ser Leu Ala Arg
545                 550                 555                 560
```

```
Ala Val Tyr Lys Asp Ala Asp Leu Tyr Leu Leu Asp Ser Pro Phe Gly
            565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu His Glu Gly Ser Ser
            610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
            645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
            675                 680                 685
Gln Thr Gly Glu Phe Gly Glu Lys Arg Lys Asn Ser Ile Leu Asn Pro
            690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
            725                 730                 735
Ser Leu Val Pro Asp Ser Glu Gln Gly Glu Ala Ile Leu Pro Arg Ile
            740                 745                 750
Ser Val Ile Ser Thr Gly Pro Thr Leu Gln Ala Arg Arg Arg Gln Ser
            755                 760                 765
Val Leu Asn Leu Met Thr His Ser Val Asn Gln Gly Gln Asn Ile His
            770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
            805                 810                 815
Gly Leu Glu Ile Ser Glu Glu Ile Asn Glu Glu Asp Leu Lys Glu Cys
            820                 825                 830
Leu Phe Asp Asp Met Glu Ser Ile Pro Ala Val Thr Thr Trp Asn Thr
            835                 840                 845
Tyr Leu Arg Tyr Ile Thr Val His Lys Ser Leu Ile Phe Val Leu Ile
            850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
            885                 890                 895
His Ser Arg Asn Asn Ser Tyr Ala Val Ile Ile Thr Ser Thr Ser Ser
            900                 905                 910
Tyr Tyr Val Phe Tyr Ile Tyr Val Gly Val Ala Asp Thr Leu Leu Ala
            915                 920                 925
Met Gly Phe Phe Arg Gly Leu Pro Leu Val His Thr Leu Ile Thr Val
            930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
            965                 970                 975
```

-continued

```
Ser Lys Asp Ile Ala Ile Leu Asp Asp Leu Pro Leu Thr Ile Phe
            980                 985                 990

Asp Phe Ile Gln Leu Leu Ile Val Ile Gly Ala Ile Ala Val Val
            995                1000                1005

Ala Val Leu Gln Pro Tyr Ile Phe Val Ala Thr Val Pro Val Ile Val
      1010                1015                1020

Ala Phe Ile Met Leu Arg Ala Tyr Phe Leu Gln Thr Ser Gln Leu
1025                1030                1035                1040

Lys Gln Leu Glu Ser Glu Gly Arg Ser Pro Ile Phe Thr His Leu Val
            1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
      1075                1080                1085

Trp Phe Leu Tyr Leu Ser Thr Leu Arg Trp Phe Gln Met Arg Ile Glu
      1090                1095                1100

Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
            1125                1130                1135

Met Asn Ile Met Ser Thr Leu Gln Trp Ala Val Asn Ser Ser Ile Asp
            1140                1145                1150

Val Asp Ser Leu Met Arg Ser Val Ser Arg Val Phe Lys Phe Ile Asp
            1155                1160                1165

Met Pro Thr Glu Gly Lys Pro Thr Lys Ser Thr Lys Pro Tyr Lys Asn
            1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
            1205                1210                1215

Ala Lys Tyr Thr Glu Gly Gly Asn Ala Ile Leu Glu Asn Ile Ser Phe
      1220                1225                1230

Ser Ile Ser Pro Gly Gln Arg Val Gly Leu Leu Gly Arg Thr Gly Ser
      1235                1240                1245

Gly Lys Ser Thr Leu Leu Ser Ala Phe Leu Arg Leu Leu Asn Thr Glu
1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
            1285                1290                1295

Ser Gly Thr Phe Arg Lys Asn Leu Asp Pro Tyr Glu Gln Trp Ser Asp
            1300                1305                1310

Gln Glu Ile Trp Lys Val Ala Asp Glu Val Gly Leu Arg Ser Val Ile
      1315                1320                1325

Glu Gln Phe Pro Gly Lys Leu Asp Phe Val Leu Val Asp Gly Gly Cys
      1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
            1365                1370                1375

Asp Pro Val Thr Tyr Gln Ile Ile Arg Arg Thr Leu Lys Gln Ala Phe
            1380                1385                1390

Ala Asp Cys Thr Val Ile Leu Cys Glu His Arg Ile Glu Ala Met Leu
```

```
              1395            1400            1405
Glu Cys Gln Gln Phe Leu Val Ile Glu Glu Asn Lys Val Arg Gln Tyr
    1410            1415            1420

Asp Ser Ile Gln Lys Leu Leu Asn Glu Arg Ser Leu Phe Arg Gln Ala
1425            1430            1435            1440

Ile Ser Pro Ser Asp Arg Val Lys Leu Phe Pro His Arg Asn Ser Ser
            1445            1450            1455

Lys Cys Lys Ser Lys Pro Gln Ile Ala Ala Leu Lys Glu Glu Thr Glu
        1460            1465            1470

Glu Glu Val Gln Asp Thr Arg Leu
    1475            1480

<210> SEQ ID NO 15
<211> LENGTH: 4443
<212> TYPE: DNA
<213> ORGANISM: Homo sapiens
<220> FEATURE:
<221> NAME/KEY: gene
<222> LOCATION: (1)..(4443)

<400> SEQUENCE: 15
```

| | | | | | |
|---|---|---|---|---|---|
| atgcagaggt | cgcctctgga | aaaggccagc | gttgtctcca | aactttttt | cagctggacc | 60 |
| agaccaattt | tgaggaaagg | atacagacag | cgcctggaat | tgtcagacat | ataccaaatc | 120 |
| ccttctgttg | attctgctga | caatctatct | gaaaaattgg | aaagagaatg | ggatagagag | 180 |
| ctggcttcaa | agaaaaatcc | taaactcatt | aatgcccttc | ggcgatgttt | tttctggaga | 240 |
| tttatgttct | atggaatctt | tttatattta | ggggaagtca | ccaaagcagt | acagcctctc | 300 |
| ttactgggaa | gaatcatagc | ttcctatgac | ccggataaca | aggaggaacg | ctctatcgcg | 360 |
| atttatctag | gcataggctt | atgccttctc | tttattgtga | ggacactgct | cctacaccca | 420 |
| gccatttttg | gccttcatca | cattggaatg | cagatgagaa | tagctatgtt | tagtttgatt | 480 |
| tataagaaga | ctttaaagct | gtcaagccgt | gttctagata | aataagtat | tggacaactt | 540 |
| gttagtctcc | tttccaacaa | cctgaacaaa | tttgatgaag | gacttgcatt | ggcacatttc | 600 |
| gtgtggatcg | ctcctttgca | agtggcactc | ctcatggggc | taatctggga | gttgttacag | 660 |
| gcgtctgcct | tctgtggact | tggtttcctg | atagtccttg | cccttttttca | ggctgggcta | 720 |
| gggagaatga | tgatgaagta | cagagatcag | agagctggga | agatcagtga | aagacttgtg | 780 |
| attacctcag | aaatgattga | aaatatccaa | tctgttaagg | catactgctg | ggaagaagca | 840 |
| atggaaaaaa | tgattgaaaa | cttaagacaa | acagaactga | aactgactcg | gaaggcagcc | 900 |
| tatgtgagat | acttcaatag | ctcagccttc | ttcttctcag | ggttctttgt | ggtgtttta | 960 |
| tctgtgcttc | cctatgcact | aatcaaagga | atcatcctcc | ggaaaatatt | caccaccatc | 1020 |
| tcattctgca | ttgttctgcg | catggcggtc | actcggcaat | tccctgggc | tgtacaaaca | 1080 |
| tggtatgact | ctcttggagc | aataaacaaa | atacaggatt | tcttacaaaa | gcaagaatat | 1140 |
| aagacattgg | aatataactt | aacgactaca | gaagtagtga | tggagaatgt | aacagccttc | 1200 |
| tgggaggagg | gatttgggga | attatttgag | aaagcaaaac | aaaacaataa | caatagaaaa | 1260 |
| acttctaatg | gtgatgacag | cctcttcttc | agtaatttct | cacttcttgg | tactcctgtc | 1320 |
| ctgaaagata | ttaatttcaa | gatagaaaga | ggacagttgt | tggcggttgc | tggatccact | 1380 |
| ggagcaggca | agacttcact | tctaatgatg | attatgggag | aactggagcc | ttcagagggt | 1440 |
| aaaattaagc | acagtggaag | aatttcattc | tgttctcagt | ttcctggat | tatgcctggc | 1500 |
| accattaaag | aaaatatcat | ctttggtgtt | tcctatgatg | aatatagata | cagaagcgtc | 1560 |

-continued

```
atcaaagcat gccaactaga agaggacatc tccaagtttg cagagaaaga caatatagtt    1620
cttggagaag gtggaatcac actgagtgga ggtcaacgag caagaatttc tttagcaaga    1680
gcagtataca aagatgctga tttgtattta ttagactctc cttttggata cctagatgtt    1740
ttaacagaaa aagaaatatt tgaaagctgt gtctgtaaac tgatggctaa caaaactagg    1800
attttggtca cttctaaaat ggaacattta aagaaagctg acaaaatatt aattttgcat    1860
gaaggtagca gctattttta tgggacattt tcagaactcc aaaatctaca gccagacttt    1920
agctcaaaac tcatgggatg tgattctttc gaccaattta gtgcagaaag aagaaattca    1980
atcctaactg agaccttaca ccgtttctca ttagaaggag atgctcctgt ctcctggaca    2040
gaaacaaaaa aacaatcttt taaacagact ggagagtttg ggaaaaaag gaagaattct    2100 attctcaatc caatcaactc tatacgaaaa ttttccattg tgcaaaagac tcccttacaa    2160
atgaatggca tcgaagagga ttctgatgag cctttagaga aaggctgtc cttagtacca    2220 gattctgagc agggagaggc gatactgcct cgcatcagcg tgatcagcac tggccccacg    2280
cttcaggcac gaaggaggca gtctgtcctg aacctgatga cacactcagt taaccaaggt    2340
cagaacattc accgaaagac aacagcatcc acacgaaaag tgtcactggc ccctcaggca    2400
aacttgactg aactggatat atattcaaga aggttatctc aagaaactgg cttggaaata    2460
agtgaagaaa ttaacgaaga agacttaaag gagtgctttt ttgatgatat ggagagcata    2520
ccagcagtga ctacatggaa cacataccct cgatatatta ctgtccacaa gagcttaatt    2580
tttgtgctaa tttggtgctt agtaattttt ctggcagagg tggctgcttc tttggttgtg    2640
ctgtggctcc ttgaaacac tcctcttcaa gacaaaggga atagtactca tagtagaaat    2700
aacagctatg cagtgattat caccagcacc agttcgtatt atgtgttta catttacgtg    2760 ggagtagccg acactttgct tgctatggga ttcttcagag tctaccact ggtgcatact    2820 ctaatcacag tgtcgaaaat tttacaccac aaaatgttac attctgttct tcaagcacct    2880
atgtcaaccc tcaacacgtt gaaagcaggt gggattctta atagattctc caagatata    2940 gcaattttgg atgaccttct gcctcttacc atatttgact tcatccagtt gttattaatt    3000
gtgattggag ctatagcagt tgtcgcagtt ttacaaccct acatctttgt tgcaacagtg    3060
ccagtgatag tggcttttat tatgttgaga gcatatttcc tccaaacctc acagcaactc    3120
aaacaactgg aatctgaagg caggagtcca atttctactc atcttgttac aagcttaaaa    3180
ggactatgga cacttcgtgc cttcggacgga cagccttact ttgaaactct gttccacaaa    3240
gctctgaatt tacatactgc caactggttc ttgtacctgt caacactgcg ctggttccaa    3300
atgagaatag aaatgattt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggcctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagctt tttgagacta    3780 ctgaacactg aaggagaaat ccagatcgat ggtgtgtctt gggattcaat aactttgcaa    3840
cagtggagga aagcctttgg agtgatacca cagaaagtat ttattttttc tggaacattt    3900
```

-continued

```
agaaaaaact tggatccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
tag                                                                  4443
```

<210> SEQ ID NO 16
<211> LENGTH: 1480
<212> TYPE: PRT
<213> ORGANISM: Homo sapiens
<220> FEATURE:
<221> NAME/KEY: PEPTIDE
<222> LOCATION: (1)..(1480)

<400> SEQUENCE: 16

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255
```

```
Glu Arg Leu Val Ile Thr Ser Glu Met Ile Glu Asn Ile Gln Ser Val
            260                 265                 270

Lys Ala Tyr Cys Trp Glu Ala Met Glu Lys Met Ile Glu Asn Leu
            275                 280                 285

Arg Gln Thr Glu Leu Lys Leu Thr Arg Lys Ala Ala Tyr Val Arg Tyr
            290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
            370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
            450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
            530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
```

```
                675                 680                 685
Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070

Tyr Phe Glu Thr Leu Phe His Lys Ala Leu Asn Leu His Thr Ala Asn
        1075                1080                1085

Trp Phe Leu Tyr Leu Ser Thr Leu Arg Trp Phe Gln Met Arg Ile Glu
    1090                1095                1100
```

-continued

```
Met Ile Phe Val Ile Phe Phe Ile Ala Val Thr Phe Ile Ser Ile Leu
1105                1110                1115                1120

Thr Thr Gly Glu Gly Glu Gly Arg Val Gly Ile Ile Leu Thr Leu Ala
            1125                1130                1135

Met Asn Ile Met Ser Thr Leu Gln Trp Ala Val Asn Ser Ser Ile Asp
        1140                1145                1150

Val Asp Ser Leu Met Arg Ser Val Ser Arg Val Phe Lys Phe Ile Asp
    1155                1160                1165

Met Pro Thr Glu Gly Lys Pro Thr Lys Ser Thr Lys Pro Tyr Lys Asn
1170                1175                1180

Gly Gln Leu Ser Lys Val Met Ile Ile Glu Asn Ser His Val Lys Lys
1185                1190                1195                1200

Asp Asp Ile Trp Pro Ser Gly Gly Gln Met Thr Val Lys Asp Leu Thr
            1205                1210                1215

Ala Lys Tyr Thr Glu Gly Gly Asn Ala Ile Leu Glu Asn Ile Ser Phe
        1220                1225                1230

Ser Ile Ser Pro Gly Gln Arg Val Gly Leu Leu Gly Arg Thr Gly Ser
    1235                1240                1245

Gly Lys Ser Thr Leu Leu Ser Ala Phe Leu Arg Leu Leu Asn Thr Glu
1250                1255                1260

Gly Glu Ile Gln Ile Asp Gly Val Ser Trp Asp Ser Ile Thr Leu Gln
1265                1270                1275                1280

Gln Trp Arg Lys Ala Phe Gly Val Ile Pro Gln Lys Val Phe Ile Phe
            1285                1290                1295

Ser Gly Thr Phe Arg Lys Asn Leu Asp Pro Tyr Glu Gln Trp Ser Asp
        1300                1305                1310

Gln Glu Ile Trp Lys Val Ala Asp Glu Val Gly Leu Arg Ser Val Ile
    1315                1320                1325

Glu Gln Phe Pro Gly Lys Leu Asp Phe Val Leu Val Asp Gly Gly Cys
1330                1335                1340

Val Leu Ser His Gly His Lys Gln Leu Met Cys Leu Ala Arg Ser Val
1345                1350                1355                1360

Leu Ser Lys Ala Lys Ile Leu Leu Leu Asp Glu Pro Ser Ala His Leu
            1365                1370                1375

Asp Pro Val Thr Tyr Gln Ile Ile Arg Arg Thr Leu Lys Gln Ala Phe
        1380                1385                1390

Ala Asp Cys Thr Val Ile Leu Cys Glu His Arg Ile Glu Ala Met Leu
    1395                1400                1405

Glu Cys Gln Gln Phe Leu Val Ile Glu Glu Asn Lys Val Arg Gln Tyr
1410                1415                1420

Asp Ser Ile Gln Lys Leu Leu Asn Glu Arg Ser Leu Phe Arg Gln Ala
1425                1430                1435                1440

Ile Ser Pro Ser Asp Arg Val Lys Leu Phe Pro His Arg Asn Ser Ser
            1445                1450                1455

Lys Cys Lys Ser Lys Pro Gln Ile Ala Ala Leu Lys Glu Glu Thr Glu
        1460                1465                1470

Glu Glu Val Gln Asp Thr Arg Leu
        1475                1480

<210> SEQ ID NO 17
<211> LENGTH: 4443
<212> TYPE: DNA
<213> ORGANISM: Homo sapiens
```

```
<400> SEQUENCE: 17
atgcagaggt cgcctctgga aaaggccagc gttgtctcca aacttttttt cagctggacc      60
agaccaattt tgaggaaagg atacagacag cgcctggaat tgtcagacat ataccaaatc     120
ccttctgttg attctgctga caatctatct gaaaaattgg aaagagaatg ggatagagag     180
ctggcttcaa agaaaaatcc taaactcatt aatgcccttc ggcgatgttt tttctggaga     240
tttatgttct atggaatctt tttatattta ggggaagtca ccaaagcagt acagcctctc     300
ttactgggaa gaatcatagc ttcctatgac ccggataaca aggaggaacg ctctatcgcg     360
atttatctag gcataggctt atgccttctc tttattgtga ggacactgct cctacaccca     420
gccattttg gccttcatca cattggaatg cagatgagaa tagctatgtt tagtttgatt      480
tataagaaga ctttaaagct gtcaagccgt gttctagata aaataagtat tggacaactt     540
gttagtctcc tttccaacaa cctgaacaaa tttgatgaag acttgcatt ggcacatttc      600
gtgtggatcg ctcctttgca gtggcactc ctcatggggc taatctggga gttgttacag      660
gcgtctgcct tctgtggact tggtttcctg atagtccttg ccctttttca ggctgggcta     720
gggagaatga tgatgaagta cagagatcag agagctggga gatcagtga aagacttgtg      780
attacctcag aaatgattga aaatatccaa tctgttaagg catactgctg gaagaagca      840
atggaaaaaa tgattgaaaa cttaagacaa acagaactga aactgactcg gaaggcagcc     900
tatgtgagat acttcaatag ctcagccttc ttcttctcag ggttctttgt ggtgttttta     960
tctgtgcttc cctatgcact aatcaaagga atcatcctcc ggaaaatatt caccaccatc    1020
tcattctgca ttgttctgcg catggcggtc actcggcaat ttccctgggc tgtacaaaca    1080
tggtatgact ctcttggagc aataaacaaa atacaggatt tcttacaaaa gcaagaatat    1140
aagacattgg aatataactt aacgactaca gaagtagtga tggagaatgt aacagccttc    1200
tgggaggagg gatttgggga attatttgag aaagcaaaac aaaacaataa caatagaaaa    1260
acttctaatg gtgatgacag cctcttcttc agtaatttct cacttcttgg tactcctgtc    1320
ctgaaagata ttaatttcaa gatagaaaga ggacagtgt tggcggttgc tggatccact     1380
ggagcaggca agacttcact tctaatgatg attatgggag aactggagcc ttcagagggt    1440
aaaattaagc acagtggaag aatttcattc tgttctcagt tttcctggat tatgcctggc    1500
accattaaag aaaatatcat ctttggtgtt tcctatgatg aatatagata cagaagcgtc    1560
atcaaagcat gccaactaga agaggacatc tccaagtttg cagagaaaga caatatggtt    1620
cttggagaag gtggaatcac actgagtgga ggtcaaatgg caaaaatttc tttagcaaga    1680
gcagtataca aagatgctga tttgtattta ttagactctc cttttggata cctagatgtt    1740
ttaacagaaa aagaaatatt tgaaagctgt gtctgtaaac tgatggctaa caaaactagg    1800
atttggtca cttctaaaat ggaacattta agaaagctg acaaaatatt aattttgcat     1860
gaaggtagca gctattttta tgggacattt tcagaactcc aaaatctaca gccagacttt    1920
agctcaaaac tcatgggatg tgattctttc gaccaattta gtgcagaaag aagaaattca    1980
atcctaactg agaccttaca ccgtttctca ttagaaggag atgctcctgt ctcctggaca    2040
gaaacaaaaa aacaatcttt taaacagact ggagagtttg gggaaaaaag gaagaattct    2100
attctcaatc caatcaactc tatacgaaaa ttttccattg tgcaaaagac tcccttacaa    2160
atgaatggca tcgaagagga ttctgatgag cctttagaga aaggctgtc cttagtacca    2220
gattctgagc agggagaggc gatactgcct cgcatcagcg tgatcagcac tggccccacg    2280
cttcaggcac gaaggaggca gtctgtcctg aacctgatga cacactcagt taaccaaggt    2340
```

```
cagaacattc accgaaagac aacagcatcc acacgaaaag tgtcactggc ccctcaggca    2400
aacttgactg aactggatat atattcaaga aggttatctc aagaaactgg cttggaaata    2460
agtgaagaaa ttaacgaaga agacttaaag gagtgctttt ttgatgatat ggagagcata    2520
ccagcagtga ctacatggaa cacatacctt cgatatatta ctgtccacaa gagcttaatt    2580
tttgtgctaa tttggtgctt agtaattttt ctggcagagg tggctgcttc tttggttgtg    2640
ctgtggctcc ttggaaacac tcctcttcaa gacaaaggga atagtactca tagtagaaat    2700
aacagctatg cagtgattat caccagcacc agttcgtatt atgtgtttta catttacgtg    2760
ggagtagccg acactttgct tgctatggga ttcttcagag gtctaccact ggtgcatact    2820
ctaatcacag tgtcgaaaat tttacaccac aaaatgttac attctgttct tcaagcacct    2880
atgtcaaccc tcaacacgtt gaaagcaggt gggattctta atagattctc caaagatata    2940
gcaattttgg atgaccttct gcctcttacc atatttgact tcatccagtt gttattaatt    3000
gtgattggag ctatagcagt tgtcgcagtt ttacaaccct acatctttgt tgcaacagtg    3060
ccagtgatag tggcttttat tatgttgaga gcatatttcc tccaaacctc acagcaactc    3120
aaacaactgg aatctgaagg caggagtcca attttcactc atcttgttac aagcttaaaa    3180
ggactatgga cacttcgtgc cttcggacgg cagccttact tgaaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggcccctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga agcctttgg agtgatacca cagaaagtat ttatttttc tggaacattt    3900 agaaaaaact ggatcccta tgaacagtgg agtgatcaag aaatatgaaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctctt ccccaccgga actcaagcaa gtgcaagtct    4380
aagccccaga ttgctgctct gaaagaggag acagaagaag aggtgcaaga tacaaggctt    4440
tag                                                                 4443
```

<210> SEQ ID NO 18
<211> LENGTH: 1480
<212> TYPE: PRT
<213> ORGANISM: Homo sapiens -continued

<400> SEQUENCE: 18

```
Met Gln Arg Ser Pro Leu Glu Lys Ala Ser Val Val Ser Lys Leu Phe
 1               5                  10                  15
Phe Ser Trp Thr Arg Pro Ile Leu Arg Lys Gly Tyr Arg Gln Arg Leu
             20                  25                  30
Glu Leu Ser Asp Ile Tyr Gln Ile Pro Ser Val Asp Ser Ala Asp Asn
         35                  40                  45
Leu Ser Glu Lys Leu Glu Arg Glu Trp Asp Arg Glu Leu Ala Ser Lys
     50                  55                  60
Lys Asn Pro Lys Leu Ile Asn Ala Leu Arg Arg Cys Phe Phe Trp Arg
 65                  70                  75                  80
Phe Met Phe Tyr Gly Ile Phe Leu Tyr Leu Gly Glu Val Thr Lys Ala
                 85                  90                  95
Val Gln Pro Leu Leu Leu Gly Arg Ile Ile Ala Ser Tyr Asp Pro Asp
             100                 105                 110
Asn Lys Glu Glu Arg Ser Ile Ala Ile Tyr Leu Gly Ile Gly Leu Cys
         115                 120                 125
Leu Leu Phe Ile Val Arg Thr Leu Leu Leu His Pro Ala Ile Phe Gly
    130                 135                 140
Leu His His Ile Gly Met Gln Met Arg Ile Ala Met Phe Ser Leu Ile
145                 150                 155                 160
Tyr Lys Lys Thr Leu Lys Leu Ser Ser Arg Val Leu Asp Lys Ile Ser
                165                 170                 175
Ile Gly Gln Leu Val Ser Leu Ser Asn Asn Leu Asn Lys Phe Asp
            180                 185                 190
Glu Gly Leu Ala Leu Ala His Phe Val Trp Ile Ala Pro Leu Gln Val
        195                 200                 205
Ala Leu Leu Met Gly Leu Ile Trp Glu Leu Leu Gln Ala Ser Ala Phe
    210                 215                 220
Cys Gly Leu Gly Phe Leu Ile Val Leu Ala Leu Phe Gln Ala Gly Leu
225                 230                 235                 240
Gly Arg Met Met Met Lys Tyr Arg Asp Gln Arg Ala Gly Lys Ile Ser
                245                 250                 255
Glu Arg Leu Val Ile Thr Ser Glu Met Ile Glu Asn Ile Gln Ser Val
            260                 265                 270
Lys Ala Tyr Cys Trp Glu Glu Ala Met Glu Lys Met Ile Glu Asn Leu
        275                 280                 285
Arg Gln Thr Glu Leu Lys Leu Thr Arg Lys Ala Ala Tyr Val Arg Tyr
    290                 295                 300
Phe Asn Ser Ser Ala Phe Phe Ser Gly Phe Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
            340                 345                 350
Gln Phe Pro Trp Ala Val Gln Thr Trp Tyr Asp Ser Leu Gly Ala Ile
        355                 360                 365
Asn Lys Ile Gln Asp Phe Leu Gln Lys Gln Glu Tyr Lys Thr Leu Glu
    370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
```

```
Asn Asn Arg Lys Thr Ser Asn Gly Asp Asp Ser Leu Phe Phe Ser Asn
            420                 425                 430
Phe Ser Leu Leu Gly Thr Pro Val Leu Lys Asp Ile Asn Phe Lys Ile
        435                 440                 445
Glu Arg Gly Gln Leu Leu Ala Val Ala Gly Ser Thr Gly Ala Gly Lys
    450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
        515                 520                 525
Asp Ile Ser Lys Phe Ala Glu Lys Asp Asn Met Val Leu Gly Glu Gly
    530                 535                 540
Gly Ile Thr Leu Ser Gly Gly Gln Met Ala Lys Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
        595                 600                 605
His Leu Lys Lys Ala Asp Lys Ile Leu Ile Leu His Glu Gly Ser Ser
    610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
        675                 680                 685
Gln Thr Gly Glu Phe Gly Glu Lys Arg Lys Asn Ser Ile Leu Asn Pro
    690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
            740                 745                 750
Ser Val Ile Ser Thr Gly Pro Thr Leu Gln Ala Arg Arg Arg Gln Ser
        755                 760                 765
Val Leu Asn Leu Met Thr His Ser Val Asn Gln Gly Gln Asn Ile His
    770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
            820                 825                 830
```

-continued

```
Leu Phe Asp Asp Met Glu Ser Ile Pro Ala Val Thr Thr Trp Asn Thr
            835                 840                 845
Tyr Leu Arg Tyr Ile Thr Val His Lys Ser Leu Ile Phe Val Leu Ile
        850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
                900                 905                 910
Tyr Tyr Val Phe Tyr Ile Tyr Val Gly Val Ala Asp Thr Leu Leu Ala
            915                 920                 925
Met Gly Phe Phe Arg Gly Leu Pro Leu Val His Thr Leu Ile Thr Val
        930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
                980                 985                 990
Asp Phe Ile Gln Leu Leu Leu Ile Val Ile Gly Ala Ile Ala Val Val
            995                 1000                1005
Ala Val Leu Gln Pro Tyr Ile Phe Val Ala Thr Val Pro Val Ile Val
    1010                1015                1020
Ala Phe Ile Met Leu Arg Ala Tyr Phe Leu Gln Thr Ser Gln Gln Leu
1025                1030                1035                1040
Lys Gln Leu Glu Ser Glu Gly Arg Ser Pro Ile Phe Thr His Leu Val
                1045                1050                1055
Thr Ser Leu Lys Gly Leu Trp Thr Leu Arg Ala Phe Gly Arg Gln Pro
                1060                1065                1070
Tyr Phe Glu Thr Leu Phe His Lys Ala Leu Asn Leu His Thr Ala Asn
    1075                1080                1085
Trp Phe Leu Tyr Leu Ser Thr Leu Arg Trp Phe Gln Met Arg Ile Glu
    1090                1095                1100
Met Ile Phe Val Ile Phe Phe Ile Ala Val Thr Phe Ile Ser Ile Leu
1105                1110                1115                1120
Thr Thr Gly Glu Gly Glu Gly Arg Val Gly Ile Ile Leu Thr Leu Ala
                1125                1130                1135
Met Asn Ile Met Ser Thr Leu Gln Trp Ala Val Asn Ser Ser Ile Asp
            1140                1145                1150
Val Asp Ser Leu Met Arg Ser Val Ser Arg Val Phe Lys Phe Ile Asp
        1155                1160                1165
Met Pro Thr Glu Gly Lys Pro Thr Lys Ser Thr Lys Pro Tyr Lys Asn
    1170                1175                1180
Gly Gln Leu Ser Lys Val Met Ile Ile Glu Asn Ser His Val Lys Lys
1185                1190                1195                1200
Asp Asp Ile Trp Pro Ser Gly Gly Gln Met Thr Val Lys Asp Leu Thr
                1205                1210                1215
Ala Lys Tyr Thr Glu Gly Gly Asn Ala Ile Leu Glu Asn Ile Ser Phe
            1220                1225                1230
Ser Ile Ser Pro Gly Gln Arg Val Gly Leu Leu Gly Arg Thr Gly Ser
        1235                1240                1245
Gly Lys Ser Thr Leu Leu Ser Ala Phe Leu Arg Leu Leu Asn Thr Glu
```

Gly Glu Ile Gln Ile Asp Gly Val Ser Trp Asp Ser Ile Thr Leu Gln
1265                  1270                  1275                  1280

Gln Trp Arg Lys Ala Phe Gly Val Ile Pro Gln Lys Val Phe Ile Phe
            1285                  1290                  1295

Ser Gly Thr Phe Arg Lys Asn Leu Asp Pro Tyr Glu Gln Trp Ser Asp
            1300                  1305                  1310

Gln Glu Ile Trp Lys Val Ala Asp Glu Val Gly Leu Arg Ser Val Ile
            1315                  1320                  1325

Glu Gln Phe Pro Gly Lys Leu Asp Phe Val Leu Val Asp Gly Gly Cys
            1330                  1335                  1340

Val Leu Ser His Gly His Lys Gln Leu Met Cys Leu Ala Arg Ser Val
1345                  1350                  1355                  1360

Leu Ser Lys Ala Lys Ile Leu Leu Leu Asp Glu Pro Ser Ala His Leu
            1365                  1370                  1375

Asp Pro Val Thr Tyr Gln Ile Ile Arg Arg Thr Leu Lys Gln Ala Phe
            1380                  1385                  1390

Ala Asp Cys Thr Val Ile Leu Cys Glu His Arg Ile Glu Ala Met Leu
1395                  1400                  1405

Glu Cys Gln Gln Phe Leu Val Ile Glu Glu Asn Lys Val Arg Gln Tyr
    1410                  1415                  1420

Asp Ser Ile Gln Lys Leu Leu Asn Glu Arg Ser Leu Phe Arg Gln Ala
1425                  1430                  1435                  1440

Ile Ser Pro Ser Asp Arg Val Lys Leu Phe Pro His Arg Asn Ser Ser
                1445                  1450                  1455

Lys Cys Lys Ser Lys Pro Gln Ile Ala Ala Leu Lys Glu Glu Thr Glu
            1460                  1465                  1470

Glu Glu Val Gln Asp Thr Arg Leu
        1475                  1480

<210> SEQ ID NO 19
<211> LENGTH: 4443
<212> TYPE: DNA
<213> ORGANISM: Homo sapiens

<400> SEQUENCE: 19

| | |
|---|---|
| atgcagaggt cgcctctgga aaaggccagc gttgtctcca acttttttt cagctggacc | 60 |
| agaccaattt tgaggaaagg atacagacag cgcctggaat tgtcagacat ataccaaatc | 120 |
| ccttctgttg attctgctga caatctatct gaaaaattgg aaagagaatg ggatagagag | 180 |
| ctggcttcaa agaaaaatcc taaactcatt aatgcccttc ggcgatgttt tttctggaga | 240 |
| tttatgttct atggaatctt tttatattta ggggaagtca ccaaagcagt acagcctctc | 300 |
| ttactgggaa gaatcatagc ttcctatgac ccgataaca aggaggaacg ctctatcgcg | 360 |
| atttatctag gcataggctt atgccttctc tttattgtga ggacactgct cctacaccca | 420 |
| gccattttg gccttcatca cattggaatg cagatgagaa tagctatgtt tagtttgatt | 480 |
| tataagaaga ctttaaagct gtcaagccgt gttctagata aataagtat tggacaactt | 540 |
| gttagtctcc tttccaacaa cctgaacaaa tttgatgaag acttgcatt ggcacatttc | 600 |
| gtgtggatcg ctcctttgca agtggcactc ctcatggggc taatctggga gttgttacag | 660 |
| gcgtctgcct tctgtggact tggtttcctg atagtccttg ccctttttca ggctgggcta | 720 |
| gggagaatga tgatgaagta cagagatcag agagctggga gatcagtga aagacttgtg | 780 |
| attacctcag aaatgattga aaatatccaa tctgttaagg catactgctg ggaagaagca | 840 |

-continued

```
atggaaaaaa tgattgaaaa cttaagacaa acagaactga aactgactcg gaaggcagcc      900
tatgtgagat acttcaatag ctcagccttc ttcttctcag ggttcttgt ggtgttttta       960 tctgtgcttc cctatgcact aatcaaagga atcatcctcc ggaaaatatt caccaccatc     1020
tcattctgca ttgttctgcg catggcggtc actcggcaat ttccctgggc tgtacaaaca     1080
tggtatgact ctcttggagc aataaacaaa atacaggatt tcttacaaaa gcaagaatat    1140
aagacattgg aatataactt aacgactaca gaagtagtga tggagaatgt aacagccttc    1200
tgggaggagg gatttgggga attatttgag aaagcaaaac aaaacaataa aatagaaaa    1260 acttctaatg gtgatgacag cctcttcttc agtaatttct cacttcttgg tactcctgtc    1320
ctgaaagata ttaatttcaa gatagaaaga ggacagttgt tggcggttgc tggatccact    1380
ggagcaggca agacttcact tctaatgatg attatgggag aactggagcc ttcagagggt    1440
aaaattaagc acagtggaag aatttcattc tgttctcagt tttcctggat tatgcctggc    1500
accattaaag aaaatatcat ctttggtgtt tcctatgatg aatatagata cagaagcgtc    1560
atcaaagcat gccaactaga agaggacatc tccaagtttg cagagaaaga caatatggtt    1620
cttggagaag gtggaatcac actgagtgaa ggtcaacgag caagaatttc tttagcaaga    1680
gcagtataca aagatgctga tttgtattta ttagactctc cttttggata cctagatgtt    1740
ttaacagaaa agaaatatt tgaaagctgt gtctgtaaac tgatggctaa caaaactagg    1800
attttggtca cttctaaaat ggaacattta agaaagctg acaaaatatt aattttgcat    1860
gaaggtagca gctattttta tgggacattt tcagaactcc aaaatctaca gccagacttt    1920
agctcaaaac tcatgggatg tgattctttc gaccaattta gtgcagaaag aagaaattca    1980
atcctaactg agaccttaca ccgtttctca ttagaaggag atgctcctgt ctcctggaca    2040
gaaacaaaaa aacaatcttt taaacagact ggagagtttg gggaaaaaag gaagaattct    2100
attctcaatc caatcaactc tatacgaaaa ttttccattg tgcaaaagac tcccttacaa    2160
atgaatggca tcgaagagga ttctgatgag ccttagaga gaaggctgtc cttagtacca    2220
gattctgagc agggagaggc gatactgcct cgcatcagcg tgatcagcac tggccccacg    2280
cttcaggcac gaaggaggca gtctgtcctg aacctgatga cacactcagt taaccaaggt    2340
cagaacattc accgaaagac aacagcatcc acacgaaaag tgtcactggc ccctcaggca    2400
aacttgactg aactggatat atattcaaga aggttatctc aagaaactgg cttggaaata    2460
agtgaagaaa ttaacgaaga agacttaaag gagtgctttt tgatgatat ggagagcata    2520 ccagcagtga ctacatggaa cacataccct cgatatatta ctgtccacaa gagcttaatt    2580
tttgtgctaa tttggtgctt agtaattttt ctggcagagg tggctgcttc tttggttgtg    2640
ctgtggctcc ttggaaacac tcctcttcaa gacaaaggga atagtactca tagtagaaat    2700
aacagctatg cagtgattat caccagcacc agttcgtatt atgtgtttta catttacgtg    2760
ggagtagccg acactttgct tgctatggga ttcttcagag gtctaccact ggtgcatact    2820
ctaatcacag tgtcgaaaat tttacaccac aaaatgttac attctgttct tcaagcacct    2880
atgtcaaccc tcaacacgtt gaaagcaggt gggattctta atagattctc caaagatata    2940
gcaattttgg atgaccttct gcctcttacc atatttgact tcatccagtt gttattaatt    3000
gtgattggag ctatagcagt tgtcgcagtt ttacaaccct acatctttgt tgcaacagtg    3060
ccagtgatag tggcttttat tatgttgaga gcatatttcc tccaaacctc acagcaactc    3120
aaacaactgg aatctgaagg caggagtcca attttcactc atcttgttac aagcttaaaa    3180
```

-continued

```
ggactatgga cacttcgtgc cttcggacgg cagccttact ttgaaactct gttccacaaa      3240
gctctgaatt tacatactgc caactggttc ttgtacctgt caacactgcg ctggttccaa      3300
atgagaatag aaatgatttt tgtcatcttc ttcattgctg ttaccttcat ttccatttta      3360
acaacaggag aaggagaagg aagagttggt attatcctga ctttagccat gaatatcatg      3420
agtacattgc agtgggctgt aaactccagc atagatgtgg atagcttgat gcgatctgtg      3480
agccgagtct ttaagttcat tgacatgcca acagaaggta aacctaccaa gtcaaccaaa      3540
ccatacaaga atggccaact ctcgaaagtt atgattattg agaattcaca cgtgaagaaa      3600
gatgacatct ggccctcagg gggccaaatg actgtcaaag atctcacagc aaaatacaca      3660
gaaggtggaa atgccatatt agagaacatt tccttctcaa taagtcctgg ccagagggtg      3720
ggcctcttgg gaagaactgg atcagggaag agtactttgt tatcagcttt tttgagacta      3780
ctgaacactg aaggagaaat ccagatcgat ggtgtgtctt gggattcaat aactttgcaa      3840
cagtggagga aagcctttgg agtgatacca cagaaagtat ttattttttc tggaacattt      3900
agaaaaaact tggatcccta tgaacagtgg agtgatcaag aaatatggaa agttgcagat      3960
gaggttgggc tcagatctgt gatagaacag tttcctggga agcttgactt tgtccttgtg      4020
gatgggggct gtgtcctaag ccatggccac aagcagttga tgtgcttggc tagatctgtt      4080
ctcagtaagg cgaagatctt gctgcttgat gaacccagtg ctcatttgga tccagtaaca      4140
taccaaataa ttagaagaac tctaaaacaa gcatttgctg attgcacagt aattctctgt      4200
gaacacagga tagaagcaat gctggaatgc caacaatttt tggtcataga agagaacaaa      4260
gtgcggcagt acgattccat ccagaaactg ctgaacgaga ggagcctctt ccggcaagcc      4320
atcagcccct ccgacagggt gaagctcttt ccccaccgga actcaagcaa gtgcaagtct      4380
aagccccaga ttgctgctct gaaagaggag acagaagaag aggtgcaaga tacaaggctt      4440
tag                                                                    4443
```

<210> SEQ ID NO 20
<211> LENGTH: 1480
<212> TYPE: PRT
<213> ORGANISM: Homo sapiens

<400> SEQUENCE: 20

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140
```

```
Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
        290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
        450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Met Val Leu Gly Glu Gly
        530                 535                 540

Gly Ile Thr Leu Ser Glu Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
```

-continued

```
                565                 570                 575
Tyr Leu Asp Val Leu Thr Glu Lys Glu Ile Phe Glu Ser Cys Val Cys
                580                 585                 590
Lys Leu Met Ala Asn Lys Thr Arg Ile Leu Val Thr Ser Lys Met Glu
                595                 600                 605
His Leu Lys Lys Ala Asp Lys Ile Leu Ile Leu His Glu Gly Ser Ser
                610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
                660                 665                 670
Gly Asp Ala Pro Val Ser Trp Thr Glu Thr Lys Lys Gln Ser Phe Lys
                675                 680                 685
Gln Thr Gly Glu Phe Gly Glu Lys Arg Lys Asn Ser Ile Leu Asn Pro
                690                 695                 700
Ile Asn Ser Ile Arg Lys Phe Ser Ile Val Gln Lys Thr Pro Leu Gln
705                 710                 715                 720
Met Asn Gly Ile Glu Glu Asp Ser Asp Glu Pro Leu Glu Arg Arg Leu
                725                 730                 735
Ser Leu Val Pro Asp Ser Glu Gln Gly Glu Ala Ile Leu Pro Arg Ile
                740                 745                 750
Ser Val Ile Ser Thr Gly Pro Thr Leu Gln Ala Arg Arg Arg Gln Ser
                755                 760                 765
Val Leu Asn Leu Met Thr His Ser Val Asn Gln Gly Gln Asn Ile His
                770                 775                 780
Arg Lys Thr Thr Ala Ser Thr Arg Lys Val Ser Leu Ala Pro Gln Ala
785                 790                 795                 800
Asn Leu Thr Glu Leu Asp Ile Tyr Ser Arg Arg Leu Ser Gln Glu Thr
                805                 810                 815
Gly Leu Glu Ile Ser Glu Glu Ile Asn Glu Glu Asp Leu Lys Glu Cys
                820                 825                 830
Leu Phe Asp Asp Met Glu Ser Ile Pro Ala Val Thr Thr Trp Asn Thr
                835                 840                 845
Tyr Leu Arg Tyr Ile Thr Val His Lys Ser Leu Ile Phe Val Leu Ile
                850                 855                 860
Trp Cys Leu Val Ile Phe Leu Ala Glu Val Ala Ala Ser Leu Val Val
865                 870                 875                 880
Leu Trp Leu Leu Gly Asn Thr Pro Leu Gln Asp Lys Gly Asn Ser Thr
                885                 890                 895
His Ser Arg Asn Asn Ser Tyr Ala Val Ile Ile Thr Ser Thr Ser Ser
                900                 905                 910
Tyr Tyr Val Phe Tyr Ile Tyr Val Gly Val Ala Asp Thr Leu Leu Ala
                915                 920                 925
Met Gly Phe Phe Arg Gly Leu Pro Leu Val His Thr Leu Ile Thr Val
                930                 935                 940
Ser Lys Ile Leu His His Lys Met Leu His Ser Val Leu Gln Ala Pro
945                 950                 955                 960
Met Ser Thr Leu Asn Thr Leu Lys Ala Gly Gly Ile Leu Asn Arg Phe
                965                 970                 975
Ser Lys Asp Ile Ala Ile Leu Asp Asp Leu Leu Pro Leu Thr Ile Phe
                980                 985                 990
```

-continued

```
Asp Phe Ile Gln Leu Leu Leu Ile Val Ile Gly Ala Ile Ala Val Val
        995                 1000                1005
Ala Val Leu Gln Pro Tyr Ile Phe Val Ala Thr Val Pro Val Ile Val
    1010                1015                1020
Ala Phe Ile Met Leu Arg Ala Tyr Phe Leu Gln Thr Ser Gln Gln Leu
1025                1030                1035                1040
Lys Gln Leu Glu Ser Glu Gly Arg Ser Pro Ile Phe Thr His Leu Val
            1045                1050                1055
Thr Ser Leu Lys Gly Leu Trp Thr Leu Arg Ala Phe Gly Arg Gln Pro
            1060                1065                1070
Tyr Phe Glu Thr Leu Phe His Lys Ala Leu Asn Leu His Thr Ala Asn
    1075                1080                1085
Trp Phe Leu Tyr Leu Ser Thr Leu Arg Trp Phe Gln Met Arg Ile Glu
    1090                1095                1100
Met Ile Phe Val Ile Phe Phe Ile Ala Val Thr Phe Ile Ser Ile Leu
1105                1110                1115                1120
Thr Thr Gly Glu Gly Glu Gly Arg Val Gly Ile Ile Leu Thr Leu Ala
            1125                1130                1135
Met Asn Ile Met Ser Thr Leu Gln Trp Ala Val Asn Ser Ser Ile Asp
            1140                1145                1150
Val Asp Ser Leu Met Arg Ser Val Ser Arg Val Phe Lys Phe Ile Asp
    1155                1160                1165
Met Pro Thr Glu Gly Lys Pro Thr Lys Ser Thr Lys Pro Tyr Lys Asn
    1170                1175                1180
Gly Gln Leu Ser Lys Val Met Ile Ile Glu Asn Ser His Val Lys Lys
1185                1190                1195                1200
Asp Asp Ile Trp Pro Ser Gly Gly Gln Met Thr Val Lys Asp Leu Thr
            1205                1210                1215
Ala Lys Tyr Thr Glu Gly Gly Asn Ala Ile Leu Glu Asn Ile Ser Phe
            1220                1225                1230
Ser Ile Ser Pro Gly Gln Arg Val Gly Leu Leu Gly Arg Thr Gly Ser
    1235                1240                1245
Gly Lys Ser Thr Leu Leu Ser Ala Phe Leu Arg Leu Leu Asn Thr Glu
1250                1255                1260
Gly Glu Ile Gln Ile Asp Gly Val Ser Trp Asp Ser Ile Thr Leu Gln
1265                1270                1275                1280
Gln Trp Arg Lys Ala Phe Gly Val Ile Pro Gln Lys Val Phe Ile Phe
            1285                1290                1295
Ser Gly Thr Phe Arg Lys Asn Leu Asp Pro Tyr Glu Gln Trp Ser Asp
            1300                1305                1310
Gln Glu Ile Trp Lys Val Ala Asp Glu Val Gly Leu Arg Ser Val Ile
        1315                1320                1325
Glu Gln Phe Pro Gly Lys Leu Asp Phe Val Leu Val Asp Gly Gly Cys
1330                1335                1340
Val Leu Ser His Gly His Lys Gln Leu Met Cys Leu Ala Arg Ser Val
1345                1350                1355                1360
Leu Ser Lys Ala Lys Ile Leu Leu Leu Asp Glu Pro Ser Ala His Leu
            1365                1370                1375
Asp Pro Val Thr Tyr Gln Ile Ile Arg Arg Thr Leu Lys Gln Ala Phe
            1380                1385                1390
Ala Asp Cys Thr Val Ile Leu Cys Glu His Arg Ile Glu Ala Met Leu
            1395                1400                1405
```

-continued

```
Glu Cys Gln Gln Phe Leu Val Ile Glu Asn Lys Val Arg Gln Tyr
    1410                1415                1420

Asp Ser Ile Gln Lys Leu Leu Asn Arg Ser Leu Phe Arg Gln Ala
1425            1430                1435                1440

Ile Ser Pro Ser Asp Arg Val Lys Leu Phe Pro His Arg Asn Ser Ser
            1445                1450                1455

Lys Cys Lys Ser Lys Pro Gln Ile Ala Ala Leu Lys Glu Glu Thr Glu
            1460                1465                1470

Glu Glu Val Gln Asp Thr Arg Leu
    1475                1480
```

CFTR GENES AND PROTEINS FOR CYSTIC FIBROSIS GENE THERAPY

CROSS-REFERENCE TO A RELATED APPLICATION

This application claims priority from provisional application U.S. Ser. No. 60/105,444, filed Oct. 23, 1998.

The subject invention was made with government support under a research project supported by NIH Grant No. HL61234. The government has certain rights in this invention.

FIELD OF INVENTION

The present invention relates to CFTR genes encoding mutant CFTR proteins that result in greater chloride channel activity than the wildtype CFTR gene and protein, when expressed in mammalian cells. These genes can be used advantageously in place of the wildtype CFTR gene for treatment of cystic fibrosis by gene therapy.

BACKGROUND OF THE INVENTION

Cystic fibrosis (CF) is the most common genetic disease of Caucasians in North America, occurring at a frequency of approximately 1 in 2500 births. Boat et al. (1989) and Welsh et al. (1993) review cystic fibrosis and the molecular basis of the disease. The disease results from defective function of the gene encoding the Cystic Fibrosis Transmembrane Conductance Regulator (CFTR) protein in a variety of tissues, including the pancreas and the lung epithelium. Riordan et al. (1989), Rommens et al. (1989) and Kerem et al. (1989) describe the cloning and sequencing of the CFTR gene. U.S. Pat. No. 5,543,399 to Riordan et al. discloses the purification of CFTR protein.

The absence of CFTR protein in the pancreatic duct results in the blockage of the duct by a thick mucus that prevents pancreatic enzymes from passing from the pancreas to the intestine. Without treatment, CF patients decline as a consequence of malnutrition associated with insufficient pancreatic function. However, pancreatic enzymes may be introduced into the diet of CF patients as a means of reversing the effects of pancreatic insufficiency.

Unlike in the pancreas, the absence of CFTR function in lung epithelium results in a severe lung disease that cannot be readily reversed or controlled by conventional treatment. Lack of CFTR function in the lung results in airway fluid with an altered ion composition, thereby creating a favorable environment for disease-causing bacteria to colonize the lung. Additionally, mucus secreted into the lung becomes thick and viscous, preventing normal clearing of the bacteria from the airways. The chronic bacterial infection leads to destruction of lung tissue and loss of lung function. Current treatments for CF lung disease involve physical therapy to aid mucus clearance and antibiotic therapy to treat the lung infection. Although these treatments slow the progression of disease, they do not reverse it. Patients with CF consequently die prematurely, usually by the age of 30.

Gene therapy may provide an alternative to conventional therapies for the treatment of cystic fibrosis. CF cells lack CFTR chloride channel activity because they have mutant CFTR genes encoding defective CFTR protein. Gene therapy strategies for the treatment of CF thus involve delivery of a wildtype human CFTR cDNA gene to mutant CF epithelial cells within the lung to restore normal CFTR chloride channel activity. U.S. Pat. No. 5,240,846 to Collin et al. discloses viral and plasmid vectors for CF gene therapy. Rosenfeld et al. (1992), Grubb et al. (1994), Teramoto et al. and Zabner et al. (1993, 1994a and 1994b) describe the use of Adenovirus to transfer the CFTR gene to airway epithelial cells. Gene transfer of the CFTR gene may occur by several different delivery methods. Viral vectors provide an efficient means to deliver the CFTR gene to CF cells, and allow correction of the chloride channel defect in cells infected with recombinant virus containing the wildtype CFTR gene. Recombinant adenovirus containing the wildtype CFTR gene have been shown to efficiently transfer the wildtype CFTR gene into CF epithelium, and correct the $Cl^-$ channel defect. U.S. Pat. No. 5,670,488 discloses Adenovirus vectors for gene therapy. However, high doses of virus are generally required to obtain an efficacious response, and the high doses of virus cause inflammation resulting from the immune response to the viral proteins. Other viruses that may be used for CF gene therapy include AAV (Adeno-associated virus), retrovirus and lentivirus. Flotte et al. (1993) describe the use of AAV in cystic fibrosis gene therapy. The use of these viruses for gene therapy is also limited by immune response to the high titer doses required for an efficacious response.

Gene transfer can also be achieved by transfection of CF cells by lipid-DNA complexes composed of plasmid DNA containing the CFTR cDNA in association with cationic or neutral lipids. Jiang et al. (1998) and Alton et al. (1999) describe the use of cationic lipids for cystic fibrosis gene therapy. Gene therapy utilizing lipid-DNA complexes is a potential alternative to the use of viral vectors and presents a lower risk for an associated inflammatory immune response. However, gene transfer with lipid-DNA complexes is inefficient, so that only a small fraction of cells receive the therapeutic gene. As a consequence, only a very limited correction of the chloride channel defect is possible. Because the efficiency of conventional gene transfer is low, a more substantial correction of the defect would be possible if a CFTR gene were used that was capable of providing higher functional activity than the wildtype CFTR gene. However, there are no currently known means for increasing functional activity of CFTR proteins.

BRIEF SUMMARY OF THE INVENTION

The present invention concerns mutated CFTR genes encoding modified CFTR proteins that result in increased CFTR chloride channel functions in comparison to wildtype CFTR. The modified CFTR proteins of the invention comprise at least one amino acid substitution based on the wildtype CFTR sequence. In a specific embodiment, an amino acid substitution of isoleucine at position 539 to either threonine (I539T) or methionine (I539M) results in increased CFTR chloride channel function, as compared to the wildtype CFTR gene, when expressed in mammalian cells. In another embodiment, glycine at position 550 is substituted with a glutamic acid (G550E). Substitution of amino acids at multiple sites in the CFTR protein is also contemplated in the present invention. The modified CFTR proteins are also an aspect of the subject invention.

The subject invention also concerns methods for increasing CFTR-mediated chloride channel activity in a cell by expressing a polynucleotide encoding a modified CFTR protein of the invention in a target cell.

The subject invention also concerns methods for treating patients with deficiencies in CFTR function. In one embodiment, the modified CFTR genes of the present invention can be used as a therapeutic agent delivered to CF cells by gene therapy. The modified CFTR genes of the present invention provide CFTR proteins with higher CFTR channel activity than that achievable with gene transfer of the wildtype CFTR gene. In a preferred embodiment, the modified CFTR gene encodes a CFTR protein having an amino acid substitution(s) contemplated by the subject invention. Because expression of the modified CFTR protein encoded by the gene results in higher CFTR channel activity, fewer target cells need to be transfected in order to obtain a sufficient correction of the chloride secretion defect.

BRIEF DESCRIPTION OF SEQUENCES

Figure 1:
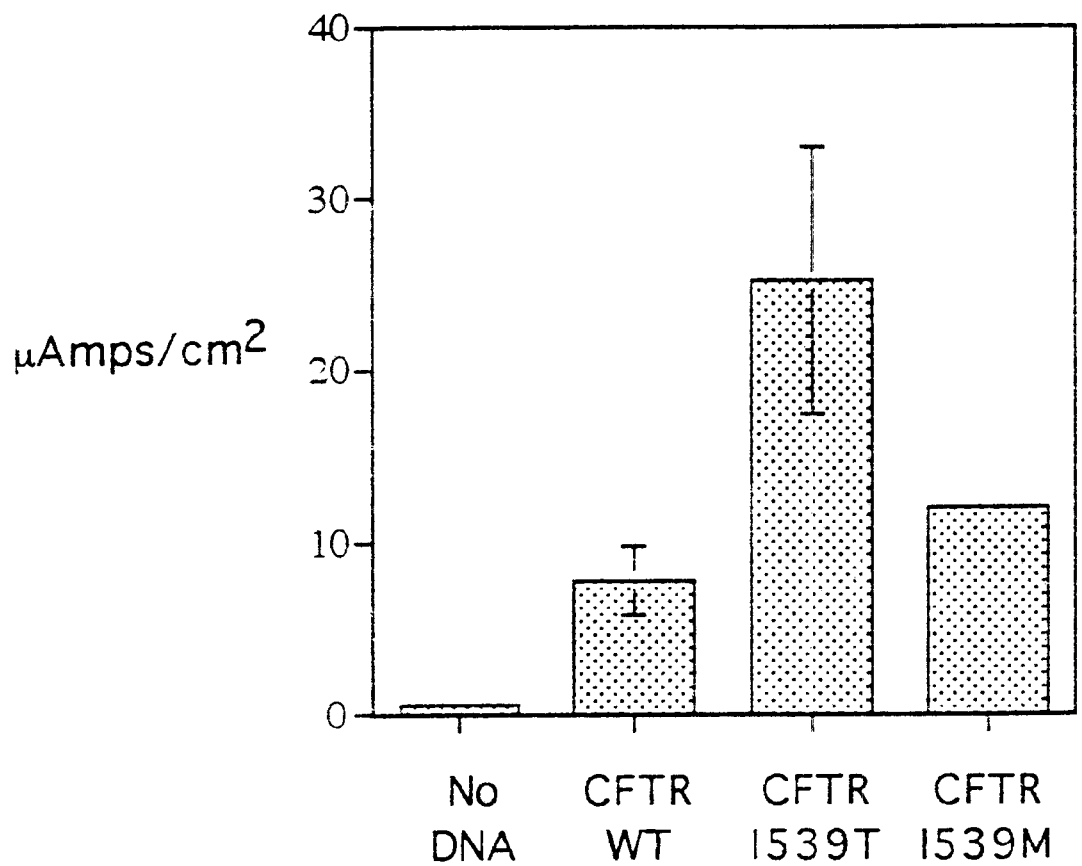
FIG. 1 shows the cAMP-stimulated Cl⁻ current associated with expression of the wildtype CFTR gene (CFTR-WT), a CFTR gene containing the I539T mutation (SEQ ID NO. 1), and a CFTR gene containing the I539M mutation (SEQ ID NO. 3) in transfected Fisher Rat Thyroid monolayers.
Figure 2:
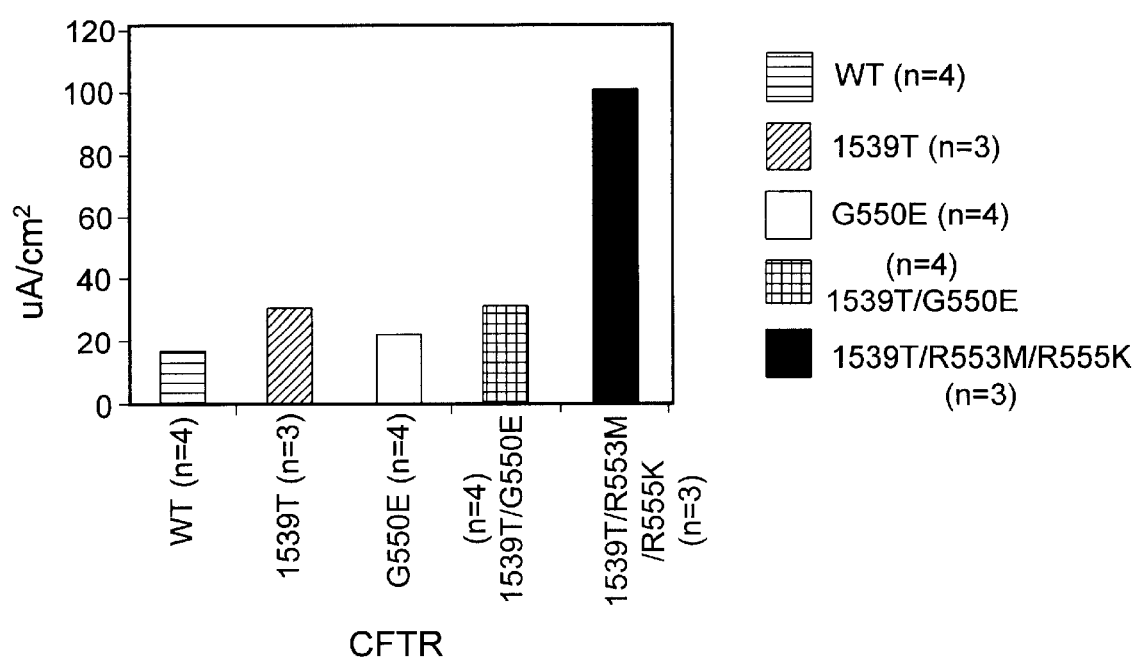
FIG. 2 shows the cAMP-stimulated Cl⁻ current associated with expression of the wildtype CFTR gene (CFTR-WT), a CFTR gene containing the I539T mutation (SEQ ID NO. 1), a CFTR gene containing the G550E mutation (SEQ ID NO. 5), a CFTR gene containing the I539T/G550E double mutation (SEQ ID NO. 7) or a CFTR gene containing the I539T/R553M/R555K triple mutation (SEQ ID NO. 9) in transfected Fisher Rat Thyroid monolayers.

SEQ ID NO. 1 is a polynucleotide sequence that encodes a CFTR protein wherein the amino acid at position 539 of the wildtype sequence is replaced by a threonine.

SEQ ID NO. 2 is an amino acid sequence of a CFTR protein wherein the amino acid at position 539 of the wildtype sequence is replaced by a threonine.

SEQ ID NO. 3 is a polynucleotide sequence that encodes a CFTR protein wherein the amino acid at position 539 of the wildtype sequence is replaced by a methionine.

SEQ ID NO. 4 is an amino acid sequence of a CFTR protein wherein the amino acid at position 539 of the wildtype sequence is replaced by a methionine.

SEQ ID NO. 5 is a polynucleotide sequence that encodes a CFTR protein wherein the amino acid at position 550 of the wildtype sequence is. replaced by glutamic acid.

SEQ ID NO. 6 is an amino acid sequence of a CFTR protein wherein the amino acid at position 550 of the wildtype sequence is replaced by glutamic acid.

SEQ ID NO. 7 is a polynucleotide sequence that encodes a CFTR protein wherein the amino acid at position 553 of the wildtype sequence is replaced by a methionine.

SEQ ID NO. 8 is an amino acid sequence of CFTR protein wherein the amino acid at position 553 of the wildtype sequence is replaced by a methionine.

SEQ ID NO. 9 is a polynucleotide sequence that encodes a CFTR protein wherein the amino acid at position 555 of the wildtype sequence is replaced by lysine.

SEQ ID NO. 10 is an amino acid sequence of a CFTR protein wherein the amino acid at position 555 of the wildtype sequence is replaced by lysine.

SEQ ID NO. 11 is a polynucleotide sequence that encodes a CFTR protein wherein the amino acid at positions 539 and 550 of the wildtype sequence are replaced by threonine and glutamic acid, respectively.

SEQ ID NO. 12 is an amino acid sequence of a CFTR protein wherein the amino acid at positions 539 and 550 of the wildtype sequence are replaced by threonine and glutamic acid, respectively.

SEQ ID NO. 13 is a polynucleotide sequence that encodes a CFTR protein wherein the amino acid at positions 539, 553 and 555 of the wildtype sequence are replaced by threonine, methionine and lysine, respectively.

SEQ ID NO. 14 is an amino acid sequence of a CFTR protein wherein the amino acid at positions 539, 553 and 555 of the wildtype sequence are replaced by threonine, methionine and lysine, respectively.

SEQ ID NO. 15 is a polynucleotide sequence that encodes a wildtype CFTR protein.

SEQ ID NO. 16 is an amino acid sequence of a wildtype CFTR protein.

SEQ ID NO. 17 is a polynucleotide sequence that encodes a CFTR protein wherein the amino acid at positions 539, 553 and 555 of the wildtype sequence are replaced by methionine, methionine and lysine, respectively.

SEQ ID NO. 18 is an amino acid sequence of a CFTR protein wherein the amino acid at positions 539, 553 and 555 of the wildtype sequence are replaced by methionine, methionine and lysine, respectively.

SEQ ID NO. 19 is a polynucleotide sequence that encodes a CFTR protein wherein the amino acid at positions 539 and 550 of the wildtype sequence are replaced by methionine and glutamic acid, respectively.

DETAILED DISCLOSURE OF THE INVENTION

The present invention concerns mutant CFTR proteins, and the polynucleotide sequences that encode the proteins, that, when expressed in cells, result in higher CFTR channel activity as compared to the CFTR protein encoded by a wildtype CFTR gene. In one embodiment, a polynucleotide sequence encodes a modified CFTR protein that comprises at least one amino acid substitution in the sequence of the protein that when expressed in a cell provides for increased CFTR channel activity as compared to the activity observed for wildtype CFTR protein. Modified CFTR proteins having single and multiple amino acid substitutions, and the polynucleotide sequences that encode them, are exemplified. In a preferred embodiment, a polynucleotide of the present invention encodes a modified CFTR protein having at least one amino acid substitution within the human CFTR protein sequence from about amino acid residue 535 to about amino acid residue 560 in the human CFTR protein sequence. More preferably, at least one amino acid substitution is from about amino acid residue 539 to about 555.

When used as a therapeutic gene delivered to CF cells by gene therapy, a CFTR gene encoding a modified CFTR protein of the present invention will result in higher CFTR channel activity than that achievable with gene transfer of the wildtype CFTR gene. Because in vivo expression of the modified CFTR proteins encoded by the subject CFTR mutant genes results in higher CFTR channel activity, fewer target cells need to be transfected in order to obtain a sufficient correction of the chloride secretion defect.

In one embodiment of the invention, a human CFTR polynucleotide sequence encodes a CFTR protein that has the amino acid isoleucine at position 539 (I539) replaced by another amino acid. In an exemplified embodiment, the isoleucine at position 539 is replaced by a threonine (the polynucleotide sequence encoding the modified protein is referred to as CFTR-I539T, SEQ ID NO. 1). The CFTR-I539T polynucleotide sequence disclosed herein encodes a CFTR protein (SEQ ID NO. 2) that functions as a cAMP-regulated chloride channel with improved advantageous properties for use as a therapeutic gene for cystic fibrosis gene therapy as compared to wildtype CFTR protein encoded by the wildtype CFTR gene. When introduced into mammalian cells deficient in an endogenous cAMP-stimulated chloride channel, the modified protein encoded by the CFTR-I539T polynucleotide sequence results in cAMP-stimulated chloride conductance at about 3 fold higher levels than that observed for the wildtype CFTR gene. Because the chloride channel activity provided by CFTR-I539T cDNA is greater than that achievable with wildtype CFTR, a correspondingly greater correction of the cAMP-stimulated chloride channel defect in CF target cells can be attained by gene transfer of the CFTR-I539T polynucleotide sequence into mammalian target cells.

In another exemplified embodiment of the invention, a human CFTR polynucleotide sequence encodes a CFTR protein that has the amino acid isoleucine at position 539 replaced by methionine (the polynucleotide sequence encoding the modified protein is referred to as CFTR-I539M, SEQ ID NO. 3). The CFTR-I539M polynucleotide sequence disclosed herein encodes a CFTR protein (SEQ ID NO. 4) that functions as a cAMP-regulated chloride channel with improved advantageous properties for use as a therapeutic gene for cystic fibrosis gene therapy as compared to wildtype CFTR protein encoded by the wildtype CFTR gene. When introduced into mammalian cells deficient in an endogenous cAMP-stimulated chloride channel, the modified protein encoded by the CFTR-I539M polynucleotide sequence results in CFTR-I539M protein (SEQ. NO. 4) that results in cAMP-stimulated chloride conductance at about 1.5 fold higher levels than that observed for the wildtype CFTR gene.

In another embodiment of the present invention, a human CFTR polynucleotide sequence encodes a CFTR protein that has the amino acid glycine at position 550 (G550) replaced by another amino acid. In an exemplified embodiment, the glycine at position 550 is replaced by glutamic acid (the polynucleotide sequence encoding the modified protein is referred to as CFTR-G550E, SEQ ID NO. 5). This modified CFTR protein (SEQ ID NO. 6) also exhibits increased chloride channel conductance as compared to wildtype protein when expressed in mammalian cells.

The present invention also provides for mutations at multiple sites in the sequence of a single CFTR protein that results in a modified CFTR protein that exhibits increased CFTR chloride channel activity in comparison to wildtype CFTR protein when expressed in mammalian cells. In one embodiment, a double mutant CFTR contains an amino acid substitution at amino acid positions 539 and 550 of the wildtype sequence. In a preferred embodiment, the amino acid encoded at position 539 of the double mutant is threonine or methionine, and the amino acid encoded at position 550 is glutamic acid (SEQ ID NO. 12 and SEQ ID NO. 20). A polynucleotide sequence (referred to as CFTR-I539T/G550E) encoding the double mutant protein is shown in SEQ ID NO. 11. A polynucleotide sequence (referred to as CFTR-I539M/G550E) encoding the double mutant protein is shown in SEQ ID NO. 19.

In another embodiment, a triple mutant CFTR protein of the present invention contains an amino acid substitution at positions 539, 553 and 555 of the wildtype sequence. In a preferred embodiment, the amino acid encode at position 539 of the triple mutant is threonine or methionine, and the amino acids encoded at positions 553 and 555 of the modified CFTR are methionine and lysine, respectively (SEQ ID NO. 14 and SEQ ID NO. 18). A polynucleotide sequence (referred to as CFTR-I539T/R553MIR555K) encoding the triple mutant protein is shown in SEQ ID NO. 13. A polynucleotide sequence (referred to as CFTR-I539M/R553M/R555K) encoding the triple mutant protein is shown in SEQ ID NO 17.

In addition to the specific amino acids exemplified in the modified CFTR proteins of the invention, also contemplated within the scope of the invention are the use of other amino acids as long as the CFTR protein exhibits increased activity relative to wildtype. For example, amino acids may be placed in the following classes: non-polar, uncharged polar, basic and acidic. Included within the scope of the invention are conservative substitutions, whereby an amino acid of one class is replaced with an amino acid of the same class, as well as substitution of an amino acid with an amino acid of a different class. The skilled artisan, having the benefit of the teachings contained herein, can readily determine whether a CFTR protein having an amino acid substitution other than those specifically exemplified results in increased CFTR activity relative to wildtype CFTR protein.

Also contemplated within the scope of the present invention are fragments and variants of the subject polynucleotides and polypeptides. Fragments and variants falling within the scope of the invention include those fragments and variants that retain substantially the same biological activity as the full-length molecule. Such fragments and variants can easily and routinely be produced by techniques well known in the art. For example, time-controlled Bal31 exonuclease digestion of the full-length DNA followed by expression of the resulting fragments and routine screening methods can be used to readily identify expression products having the desired activity (Wei et al., 1983). U.S. Pat. No. 5,639,661 to Welsh et al. describes polynucleotide sequences encoding fragments of the full-length CFTR protein that are biologically active.

Those skilled in the art will recognize that polynucleotide sequences encoding the modified CFTR proteins of the present invention can be introduced into recombinant gene therapy vectors suitable for the treatment of cystic fibrosis. Thus, the subject invention also concerns methods for treating CF by providing cells containing defective CFTR protein with modified CFTR proteins of the subject invention. The use of recombinant vectors to express mutant CFTR genes of the invention in CF cells will result in the synthesis of modified CFTR protein that exhibits increased chloride channel activity in the CF cells and can provide for advantageous correction of defective CFTR function in the CF cell.

The subject invention also concerns expression vectors comprising a polynucleotide sequence of the present invention that encodes a modified CFTR protein having increased chloride channel activity when expressed in vivo. Preferably, the expression vectors are those vectors suitable for expression of polynucleotide sequences in human cells. Suitable expression vectors are known in the art and can be readily selected and prepared with the sequences of the present invention by the ordinarily skilled artisan having the benefit of the teachings contained herein.

The subject invention also concerns host cells containing the polynucleotide or polypeptide sequences of the present invention. The host cells can be any suitable prokaryotic or eukaryotic cell, including bacterial, yeast, insect and mammalian cells. In a preferred embodiment, the host cells are mammalian cells. More preferably, the host cells are human cells. In one embodiment, the host cells are human CF cells. Host cells can be transformed with the mutant CFTR genes according to standard methods known in the art.

The subject invention also concerns methods for increasing the CFTR-mediated chloride channel activity of a cell, said method comprising transforming a cell with an effective amount of polynucleotide of the invention and expressing that polynucleotide in the cell. In one embodiment, the cells are transformed with an expression vector comprising a polynucleotide that encodes a modified CFTR protein having an amino acid sequence selected from the following: SEQ ID NO. 2, SEQ ID NO. 4, SEQ ID NO. 6, SEQ ID NO. 8, SEQ ID NO. 10, SEQ ID NO. 12 and SEQ ID NO. 14. In a preferred embodiment, the cells are transformed with an expression vector comprising a polynucleotide sequence encoding a modified CFTR protein that contains an amino acid substitution at positions 539, 553 and 555 o the wildtype sequence. Preferably, the amino acid encoded at position 539 of the triple mutant is threonine or methionine, and the amino acids encoded at positions 553 and 555 of the modified CFTR are methionine and lysine, respectively (SEQ ID NO. 14). Cells can be transformed using standard procedures known in the art including transfection electroporation, lipofection and viral vectors, such as Adenovirus and AAV.

The subject invention also concerns methods for treating a patient having a deficiency or dysfunction in CFTR function. In one embodiment, the method comprises delivering to the cells of the patient an effective amount of polynucleotide of the invention and expressing that polynucleotide in the cells. Polynucleotides of the invention can be introduced and expressed in target cells using any standard gene therapy techniques known in the art. Examples of gene therapy methodology are described in U.S. Pat. Nos. 5,399,346; 5,670,488; 5,827,703; 5,240,846; and in published international patent application WO 93/24641. In one embodiment, the cells are transformed with an expression vector comprising a polynucleotide that encodes a modified CFTR protein having an amino acid sequence selected from the following: SEQ ID NO. 2, SEQ ID NO. 4, SEQ ID NO. 6, SEQ ID NO. 8, SEQ ID NO. 10, SEQ ID NO. 12 and SEQ ID NO. 14. In a preferred embodiment, the cells are transformed with an expression vector comprising a polynucleotide sequence encoding a modified CFTR protein that contains an amino acid substitution at positions 539, 553 and 555 of the wildtype sequence. Preferably, the amino acid encoded at position 539 of the triple mutant is threonine or methionine, and the amino acids encoded at positions 553 and 555 of the modified CFTR are methionine and lysine, respectively (SEQ ID NO. 14).

In another embodiment for treating a patient having CFTR deficiency or dysfunction, the method comprises introducing a modified CFTR protein of the invention into the membrane of targeted cells of the patient. Modified CFTR proteins can be introduced into a cell membrane using any standard protein delivery method known in the art including, for example, liposomes containing the modified CFTR protein.

The polynucleotide sequences of the present invention can be composed of RNA or DNA, and can contain modified bases. More preferably, the polynucleotide sequences are composed of DNA.

As is well known in the art, the genetic code is redundant in that certain amino acids are coded for by more than one nucleotide triplet (codon). The subject invention includes those polynucleotide sequences which encode the same amino acids using a different codon from that specifically exemplified in the sequences herein. Thus, the scope of the subject invention includes not only the specific polynucleotide sequences depicted herein, but also all equivalent polynucleotide sequences encoding polypeptides of the subject invention, and fragments and variants thereof.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

The wildtype full-length human CFTR cDNA gene obtained from plasmid pTMCFTR4 was cloned into mammalian expression vector pSwick using standard DNA cloning techniques, to produce pCFTR-WT. Swick et al. (1992) describe the use of the pSwick expression vector. Insertion of the CFTR cDNA into pSwick placed the CFTR cDNA gene under the control of an SV40-Adenovirus hybrid promoter that directs high level expression of CFTR mRNA and CFTR protein in mammalian cells. Site-directed oligonucleotide mutagenesis was then used to introduce each of the I539T and I539M mutations into the CFTR cDNA gene, producing the CFTR-I539T gene (SEQ ID NO. 1) and CFTR-I539M gene (SEQ ID NO. 3), respectively Plasmid DNA containing CFTR-I539T (pCFTR-I539T) or CFTR-I539M (pCFTR-I539M) was then used for transfection of Fisher Rat Thyroid (FRT) cell monolayers. Sheppard et al. (1993, 1994) describe the use of FRT cells to assay CFTR cAMP-stimulated chloride channel activity.

FRT cells are epithelial cells that lack an endogenous cAMP-stimulated chloride conductance, and form cell monolayers that develop high resistance. They are thus well suited for measurement of CFTR Cl⁻ channel activity in monolayers transfected with CFTR alleles and are used by those skilled in the art for this purpose. FRT cells were seeded into 12 mm diameter nitrocellulose MILLICELL-HA culture plate inserts (obtained from Millipore), at a density of $4.5 \times 10^5$ cells per MILLICELL-HA, in FRT growth media (F-12 Coon's Modification media containing 5% Fetal Bovine Serum). The cells were grown at 37° C. in 5% $CO_2$ for several days, and the resistance across the MILLICELL-HA insert monitored daily. with an EVOM Ohmmeter (Millipore). MILLICELL-HA inserts that demonstrated resistances above 1000 Ohms after several days were then used for transfection.

Lipid-DNA complexes for transfection of FRT cells were prepared using DMRIE-cholesterol lipid (obtained from Gibco) and either, pCFTR-WTplasmid DNA, PCFTR-I539T plasmid DNA, or pCFTR-I539M plasmid DNA (or no DNA as a control). DNA:lipid complexes were prepared according to the specifications of the manufacturer, by mixing 5 ug. of plasmid DNA with 15 ug. of DMRIE-cholesterol lipid producing a ratio of 1:3 (DNA:lipid) in 100 ul of serum-free FRT growth media, which was then added to the apical surface of the FRT cells within the MILLICELL-HA inserts. The cells were incubated 2 hours at 37° C., and the media containing the DNA:lipid complex was then removed and replaced with ERT growth media. Cells were then incubated at 37° C. in 5% $CO_2$, with the media changed every two days. On the sixth day, the MILLICELL-HA inserts were mounted in Ussing chambers for measurement of cAMP-stimulated chloride channel activity. A chloride gradient was established across the monolayer (4.8 mM Cl⁻ apical side/ 140 mM Cl⁻ basolateral side), and the voltage across the epithelium was clamped to 0 volts using a voltage clamp amplifier. A forskolin/IBMX cocktail was then added to the apical side (final forskolin concentration $10^{-5}$ M, final IBMX concentration $10^{-4}$ M) to activate CFTR through a cAMP-dependent pathway, and the acute change in chloride conductance was then measured in response to the cAMP agonists. The functional chloride channel activity of FRT cells transfected with CFTR-WT, CFTR-I539T, or CFTR-I539M are shown in Table 1 and in FIG. 1.

TABLE 1

| Transfected DNA | Experiment 1 $\mu$Amps/cm$^2$ | Experiment 2 $\mu$Amps/cm$^2$ | Mean $\mu$Amps/cm$^2$ | Standard Error $\mu$Amps/cm$^2$ |
|---|---|---|---|---|
| No DNA | 0.43 | 0.44 | 0.45 | 0 |
| CFTR-WT | 9.67 | 5.67 | 7.67 | 2 |
| CFTR-I539T | 33 | 17.33 | 25.16 | 7.83 |
| CFTR-I539M | 12 | 11.83 | 11.91 | 0.08 |

In the absence of transfected DNA, very low cAMP-stimulated chloride channel activity was observed in the control FRT cells. In contrast, FRT cells transfected with pCFTR-WT-produced a mean cAMP-stimulated chloride conductance of 7.67 $\mu$Amps/cm$^2$. A mean cAMP-stimulated chloride channel activity greater than wildtype CFTR was observed for ERT cells transfected with pCFTR-I539M (11.91 $\mu$Amps/cm$^2$). The highest mean cAMP-stimulated chloride conductance was observed in FRT cells transfected with CFTR-I539T (25.16 $\mu$Amps/cm$^2$). These results indicate that greater cAMP-stimulated chloride channel activity can be attained by transfection of epithelial cells with either the CFTR-I539T gene or CFTR-I539M gene, as compared to the CFTR-WT gene.

EXAMPLE 2

Cells were transfected with DNA encoding wildtype CFTR or CFTR having various amino acid substitutions (CFTR-I539T, CFTR-G550E, CFTR-I539T/G550E, and CFTR-I539T/R553M/R555K) as described in Example 1, with the following modifications. FRT cells were grown to 80% confluency in tissue culture petri dishes and trypsinized by standard procedures to produce a suspension of cells. The concentration of cells in the suspension was then adjusted to $7\times10^5$ cells/ml, and 0.4 mls aliquots of the cell suspension were placed into individual microfuge tubes. Cells within microfuge tubes were pelleted by centrifugation at 1000 g for 5 minutes and resuspended in 400 ul of DNA/lipid complex prepared as described in Example 1. The suspension of cells and DNA/lipid complex were then incubated at 37° C. for two hours while gently rotated in a tissue culture roller drum. Cells were then pelleted by centrifugation at 1000 g for 5 minutes, resuspended into FRT growth media, and used to seed MILLICELL-HA inserts. Assays for cAMP-stimulated chloride channel activity were performed as in Example 1 on the sixth day following transfection. The results are shown in Table 2.

TABLE 2

Ussing chamber 7/6/99 high Cl basolateral, no nystatin.

| Transfected DNA | average 1 ($\mu$Amps/cm$^2$) | standard deviation ($\mu$Amps/cm$^2$) |
|---|---|---|
| WT (n = 4) | 17 | 3.9 |
| I539T (n = 3) | 29.97 | 1.23 |
| G550E (n = 4) | 22.79 | 1.62 |

TABLE 2-continued

Ussing chamber 7/6/99 high Cl basolateral, no nystatin.

| Transfected DNA | average 1 ($\mu$Amps/cm$^2$) | standard deviation ($\mu$Amps/cm$^2$) |
|---|---|---|
| I539T/G550E (n = 4) | 31.29 | 4.04 |
| I539T/R553M/R555K (n = 3) | 100.67 | 3.92 |

It should be understood that the examples and embodiments described herein are for illustrative purposes only and that various modifications or changes in light thereof will be suggested to persons skilled in the art and are to be included within the spirit and purview of this application and the scope of the appended claims.

References

U.S. Pat. No. 5,543,399
U.S. Pat. No. 5,639,661
U.S. Pat. No. 5,399,346
U.S. Pat. No. 5,670,488
U.S. Pat. No. 5,827,703
U.S. Pat. No. 5,240,846
International Patent Application WO 93/24641
Alton, E. W., M. Stem, R. Farley, A. Jaffe, S. L. Chadwick, J. Phillips, J. Davies, S. N. Smith, J. Browning, M. G. Davies, M. E. Hodson, S. R. Durham, D. Li, P. K. Jeffery, M. Scallan, R. Balfour, S. J. Eastman, S. H. Cheng, A. E. Smith, D. Meeker, D. M. Geddes (1999) "Cationic lipid-mediated CFTR gene transfer to the lungs and nose of patients with cystic fibrosis: a double-blind placebo-controlled trial" Lancet 353(9157):947–954.
Boat, T. F., M. J. Welsh, A. L. Beaudet (1989) "Cystic Fibrosis. In the Metabolic Basis of Inherited Disease" C. R. Scriver, A. L. Beaudet, W. S. Sly and D. Valle, eds (New York, N.Y.: McGraw-Hill, Inc.), pp. 2649–2680.
Flotte, T. R., S. A. Afione, C. Conrad, S. A. McGrath, R. Solow, H. Oka, P. L. Zeitlin, W. B. Guggino, B. J. Carter (1993) "Stable in vivo expression of the cystic fibrosis transmembrane conductance regulator with an adeno-associated virus vector" Proc Natl Acad Sci USA 90:10613–10617.
Grubb, B. R., R. J. Pickles, H. Ye, J. R. Yankaskas, R. N. Vick, J. F. Engelhardt, J. M. Wilson, L. G. Johnson, R. C. Boucher (1994) "Inefficient gene transfer by adenovirus vector to cystic fibrosis airway epithelia of mice and humans" Nature 371 :802–806.
Jiang, C., S. P. O'Connor, S. L. Fang, K. X. Wang, J. Marshall, J. L. Williams, B. Wilburn, Y. Echelard, S. H. Cheng (1998) "Efficiency of cationic lipid-mediated transfection of polarized and differentiated airway epithelial cells in vitro and in vivo" Human Gene Therapy 9:1531–1542.
Kerem, B.-S., J. M. Rommens, J.-A. Buchanan, D. Markiewicz, T. K. Cox, A. Chakravarti, M. Buchwald, L.-C. Tsui (1989) "Identification o the Cystic Fibrosis Gene: Genetic Analysis" Science 245:1073–1080.
Riordan, J. R., J. M. Rommens, B-S Kerem, N. Alon, R. Rozmahel, Z. Grzelczak, J. Zielenski, S. Lok, N. Plavsic, J-L Chou, M. L. Drumm, M. C. lannuzzi, F. S. Collins, L.-C. Tsui (1989) "Identification of the Cystic Fibrosis Gene: Cloning and characterization of complementary DNA" Science 245:1066–1073.
Rommens, J. M., M. C. Jannuzzi, B-S Kerem, M. L. Drumm, G. Melrer, M. Dean, R. Rozmahel, J. L. Cole, D. Kennedy, N. Hidaka, M. Zsiga, M. Buchwald, J. R. Riordan, L.-C. Tsui, F. Collins (1989) "Identification of the Cystic Fibrosis gene: Chromosome walking and jumping" *Science* 245:1059–1065.

Rosenfeld, M. A., K. Yoshimura, B. C. Trapnell, K. Yoneyama, E. R. Rosenthal, W. Dalemans, M. Fukayama, J: Bargon, L. E. Stier, L. Stratford-Perricaudet, M. Perricaudet, W. B. Guggino, A. Pavirani, J-P. Lecocq, R. G. Crystal (1992) "In vivo transfer of the human cystic fibrosis transmembrane conductance regulator gene to the airway epithelium" *Cell* 68:143–155.

Sheppard, D. N., D. P. Rich, L. S. Ostedgaard, R. J. Gregory, A. E. Smith, M. J. Welsh (1993) "Mutations in CFTR associated with mild disease form Cl⁻ channels with altered pore properties" *Nature* 362:160–164.

Sheppard, D. N., M. R. Carson, L. S. Ostedgaard, G. M. Denning, M. J. Welsh (1994) "Expression of cystic fibrosis transmembrane conductance regulator in a model epithelium" *Am J Physiol* 266:405–413.

Swick, A. G., M. Janicot, T. Cheneval-Kastelic J. C. McLenithan, M. D. Lane (1992) "Promoter-cDNA-directed heterologous protein expression in *Xenopus laevis* oocytes" *Proc Natl Acad Sci USA* 89(5):1812–1816.

Teramoto, S., J. S. Bartlett, D. McCarty, X. Xiao, R. J. Samulski, R. C. Boucher (1998) "Factors influencing adeno-associated virus-mediated gene transfer to human cystic fibrosis airway epithelial cells: comparison with adenovirus vectors" *J Virol* 72:8904–8912.

Wei, C.-F., G. A. Alianell, G. H. Bencen, H. B. Gray, Jr. (1983) "Isolation and Comparison of Two Molecular Species of the BAL31 Nuclease from *Alteromonas espejiana* with Distinct Kinetic Properties" *The Journal of Biological Chemistry* 258(22):13506–13512.

Welsh, M. J., A. E. Smith (1993) "Molecular mechanisms of CFTR chloride channel dysfunction in cystic fibrosis" *Cell* 73:1251–1254.

Zabner, J., L. A. Couture, R. J. Gregory, S. M. Graham, A. E. Smith, M. J. Welsh (1993) "Adenovirus-mediated gene transfer transiently corrects the chloride transport defect in nasal epithelia of patients with cystic fibrosis" *Cell* 75:207–216.

Zabner, J. L. A. Couture, A. E. Smith, M. J. Welsh (1994a) "Correction of cAMP-stimulated fluid secretion in cystic fibrosis airway epithelia: efficiency of adenovirus-mediated gene transfer in vitro" *Human Gene Therapy* 5:585–593.

Zabner, J., D. M. Petersen, A. P. Puga, S. M. Graham, L. A. Couture, L. D. Keyes, M. J. Lukason, J. A. St. George, R. J. Gregory, A. E. Smith et al. (1994b) "Safety and efficacy of repetitive adenovirus-inediated transfer of CFTR cDNA to airway A epithelia of primates and cotton rats" *Nature Genetics* 6:75–83.

What is claimed is:

1. A polynucleotide encoding a modified CFTR protein, or a biologically active fragment thereof, wherein expression of said modified CFTR protein within a cell results in increased CFTR chloride channel activity as compared to wildtype CFTR protein, wherein said modified CFTR protein has an amino acid sequence selected from the group consisting of SEQ ID NO. 2, SEQ ID NO. 12, and SEQ ID NO. 14.

2. The polynucleotide according to claim 1, wherein said polynucleotide comprises the nlucleotide sequence shown in SEQ ID NO. 1.

3. The polynucicotide according to claim 1, wherein said polynucleotide comprises the nucleotide sequence shown in SEQ ID NO. 11.

4. The polynucleotide according to claim 1, wherein said polynucleotide comprises the nucleotide sequence shown in SEQ ID NO. 13.

5. The polynucleotide according to claim 1, wherein said modified CFTR protein has the amino acid sequence shown in SEQ ID NO. 2.

6. The polyiucteotide according to claim 1, wherein said modified CFTR protein has the amino acid sequence shown in SEQ ID NO. 12.

7. The polynucleotide according to claim 1, wherein said modified CFTR protein has the amino acid sequence shown in SEQ ID NO. 14.

8. An isolated cell comprising the polynucleotide of claim 1.

9. The cell according to claim 8, wherein said polynucleotide comprises the nucleotide sequence shown in SEQ ID NO. 1.

10. The cell according to claim 8, wherein said polynucleotide comprises the nucleotide sequence shown in SEQ ID NO. 11.

11. The cell according to claim 8, wherein said polynucleotide comprises the nucleotide sequence shown in SEQ ID NO. 13.

12. The cell according to claim 8, wherein said modified CFTR protein has the amino acid sequence shown in SEQ ID NO. 2.

13. The cell according to claim 8, wherein said modified CFTR protein has the amino acid sequence shown in SEQ ID NO. 12.

14. The cell according to claim 8, wherein said modified CFTR protein has the amino acid sequence shown in SEQ ID NO. 14.

15. The cell according to claim 8, wherein said cell is selected from the group consisting of a bacterial cell, a yeast cell, an insect cell and a mammalian cell.

16. The cell according to claim 15, wherein said mammalian cell is a human cell.

17. A polynucleotide expression vector comprising the polynucleotide of claim 1.

18. The expression vector according to claim 17, wherein said polynucleotide comprises the nucleotide sequence shown in SEQ ID NO. 1.

19. The expression vector according to claim 17, wherein said polynucleotide comprises the nucleotide sequence shown in SEQ ID NO. 11.

20. The expression vector according to claim 17, wherein said polynucleotide comprises the nucleotide sequence shown in SEQ ID NO. 13.

21. The expression vector according to claim 17, wherein said modified CFTR protein has the amino acid sequence shown in SEQ ID NO. 2.

22. The expression vector according to claim 17, wherein said modified CFTR protein has the amino acid sequence shown in SEQ ID NO. 12.

23. The expression vector according to claim 17, wherein said modified CFTR protein has the amino acid sequence shown in SEQ ID NO. 14.

24. A polynucleotide molecule encoding a modified CFTR protein, or a biologically active fragment thereof, wherein expression of said modified CFTR protein within a cell results in increased CFTR chloride channel activity as compared to wildtype CFTR protein, said modified CFTR protein comprising an amino acid substitution wherein the amino acid in the wildtype protein at position 539 is substituted with a threonine.

25. An isolated cell comprising the polynucleotide of claim 24.

26. The cell according to claim 24, wherein said cell is selected from the group consisting of a bacterial cell, a yeast cell, an insect cell and a mammalian cell.

27. The cell according to claim 26, wherein said mammalian cell is a human cell.

28. A polynucleotide expression vector comprising the polynucleotide of claim 24.

* * * * *

UNITED STATES PATENT AND TRADEMARK OFFICE
CERTIFICATE OF CORRECTION

PATENT NO. : 6,468,793 B1 Page 1 of 1
DATED : October 22, 2002
INVENTOR(S) : John L. Teem It is certified that error appears in the above-identified patent and that said Letters Patent is hereby corrected as shown below:

<u>Column 4,</u>
Line 26, "SEQ ID NO. 19 is a polynucleotide sequence that encodes a CFTR protein wherein the amino acid at positions 539 and 550 of the wildtype sequence are replaced by methionine and glutamic acid, respectively.

DETAILED DISCLOSURE OF THE INVENTION"

should read

-- SEQ ID NO. 19 is a polynucleotide sequence that encodes a CFTR protein wherein the amino acid at positions 539 and 550 of the wildtype sequence are replaced by methionine and glutamic acid, respectively.

SEQ ID NO. 20 is an amino acid sequence of a CFTR protein wherein the amino acid at position 539 and 550 of the wildtype sequence are replaced by methionine and glutamic acid, respectively.

DETAILED DISCLOSURE OF THE INVENTION --.

Signed and Sealed this

Third Day of June, 2003

JAMES E. ROGAN
*Director of the United States Patent and Trademark Office*